United States Patent
Kawabata et al.

(10) Patent No.: US 7,316,322 B2
(45) Date of Patent: Jan. 8, 2008

(54) QUALITY EVALUATION APPARATUS FOR FRUITS AND VEGETABLES

(75) Inventors: Shinichi Kawabata, Sakai (JP); Kenichi Iwami, Sakai (JP); Yoshiyuki Katayama, Sakai (JP)

(73) Assignee: Kubota Corporation, Osaka (JP)

( * ) Notice: Subject to any disclaimer, the term of this patent is extended or adjusted under 35 U.S.C. 154(b) by 192 days.

(21) Appl. No.: 10/540,742

(22) PCT Filed: Dec. 24, 2003

(86) PCT No.: PCT/JP03/16536

§ 371 (c)(1),
(2), (4) Date: Jun. 24, 2005

(87) PCT Pub. No.: WO2004/059300

PCT Pub. Date: Jul. 15, 2004

(65) Prior Publication Data

US 2006/0118726 A1 Jun. 8, 2006

(30) Foreign Application Priority Data

Dec. 24, 2002 (JP) .............................. 2002-372878
Jan. 20, 2003 (JP) .............................. 2003-011091

(51) Int. Cl.
*B07C 5/00* (2006.01)
*G01N 21/00* (2006.01)

(52) U.S. Cl. ................. 209/509; 356/237.1; 356/237.2

(58) Field of Classification Search ................. 73/627; 250/358.1; 356/237.1, 417–432; 702/81
See application file for complete search history.

(56) References Cited

U.S. PATENT DOCUMENTS 3,930,994 A * 1/1976 Conway et al. ............. 209/579
3,930,995 A * 1/1976 Paddock et al. ............ 209/698
4,139,766 A * 2/1979 Conway ........................ 377/6
4,281,933 A * 8/1981 Houston et al. ............ 356/425
4,828,387 A   5/1989 Sawyers et al.
5,210,590 A * 5/1993 Landa et al. ................ 356/319
5,729,473 A * 3/1998 Blanc et al. ................ 702/128
5,822,068 A * 10/1998 Beaudry et al. ............ 356/417
6,334,092 B1 * 12/2001 Hashimoto et al. .......... 702/81
6,512,577 B1 * 1/2003 Ozanich ....................... 356/73
6,643,599 B1 * 11/2003 Mohr et al. ................ 702/108

(Continued)

FOREIGN PATENT DOCUMENTS

JP        05-045212        2/1993

(Continued)

*Primary Examiner*—Gregory J. Toatley, Jr.
*Assistant Examiner*—Jarreas Underwood
(74) *Attorney, Agent, or Firm*—The Webb Law Firm

(57) ABSTRACT

In order to provide a quality evaluation apparatus having excellent measurement accuracy in obtaining quality evaluation values of fruits and vegetables, transmitted light from one or more measured objects is received by a photo-detective sensor of the charge storage type, charges are stored in the photo-detective sensor until a predetermined charge storage time lapses from start of the charge storage, a charge storage discharge process is repeatedly executed for releasing the charges stored in the photo-detective sensor until lapse of a predetermined discharge time, the stored charges are released when the measured object reach a position for measurement, and a measurement charge storage process is executed for storing charges to be used as photo-detective information for quality evaluation.

15 Claims, 21 Drawing Sheets

U.S. PATENT DOCUMENTS

| | | | |
|---|---|---|---|
| 6,693,274 B2 * | 2/2004 | Baird et al. | 250/221 |
| 6,754,600 B2 * | 6/2004 | Hashimoto et al. | 702/81 |
| 7,016,043 B2 * | 3/2006 | Fukumori et al. | 356/432 |
| 2001/0032807 A1 * | 10/2001 | Powell | 209/592 |

FOREIGN PATENT DOCUMENTS

| | | |
|---|---|---|
| JP | 7-063674 A | 3/1995 |
| JP | 08-005550 | 1/1996 |
| JP | 8-29333 A | 2/1996 |
| JP | 10-62337 A | 3/1998 |
| JP | 63-81226 A | 4/1998 |
| JP | 2000-162047 A | 6/2000 |
| JP | 2000-199743 A | 7/2000 |
| JP | 2002-077522 A | 3/2002 |
| JP | 2002-090301 A | 3/2002 |
| JP | 2002-107294 A | 4/2002 |
| JP | 2002-107303 A | 4/2002 |
| JP | 2002-168772 A | 6/2002 |
| JP | 2002-174592 A | 6/2002 |
| JP | 2002-181701 A | 6/2002 |

* cited by examiner

FIG.14
(a)
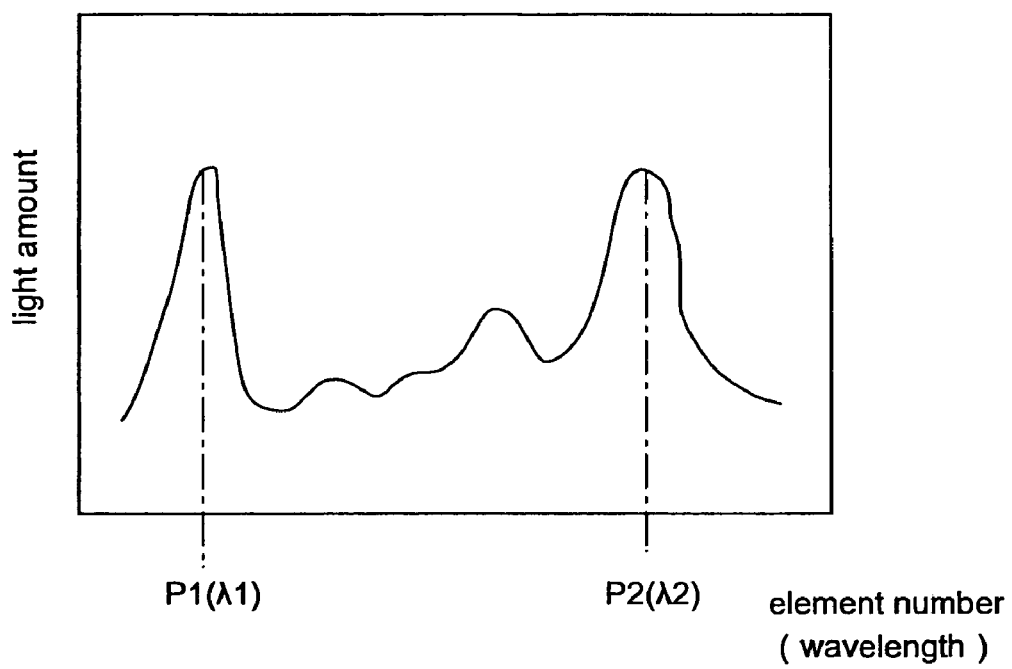
(b)
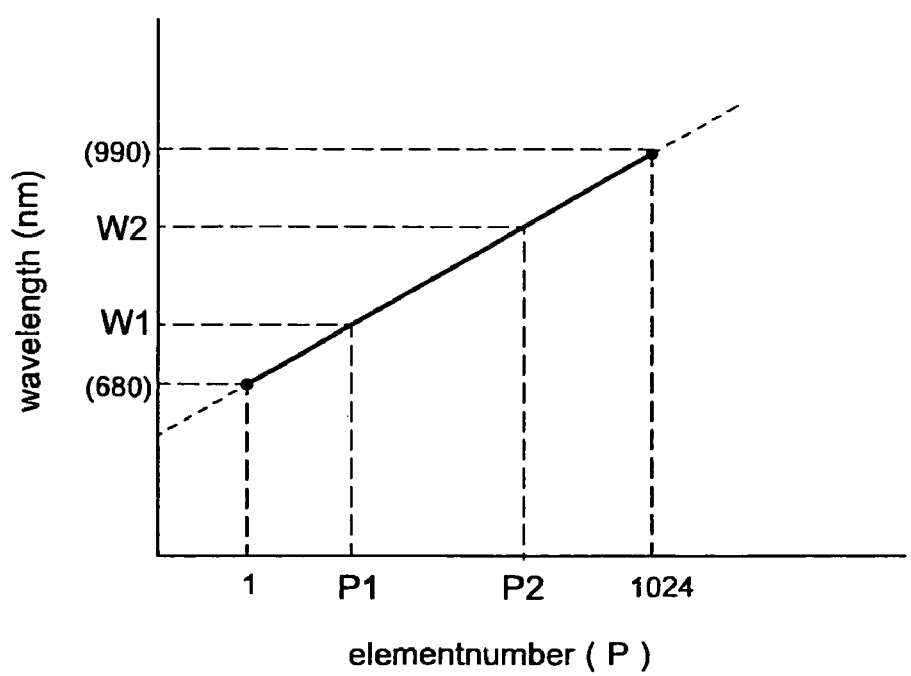

FIG.17
(a)
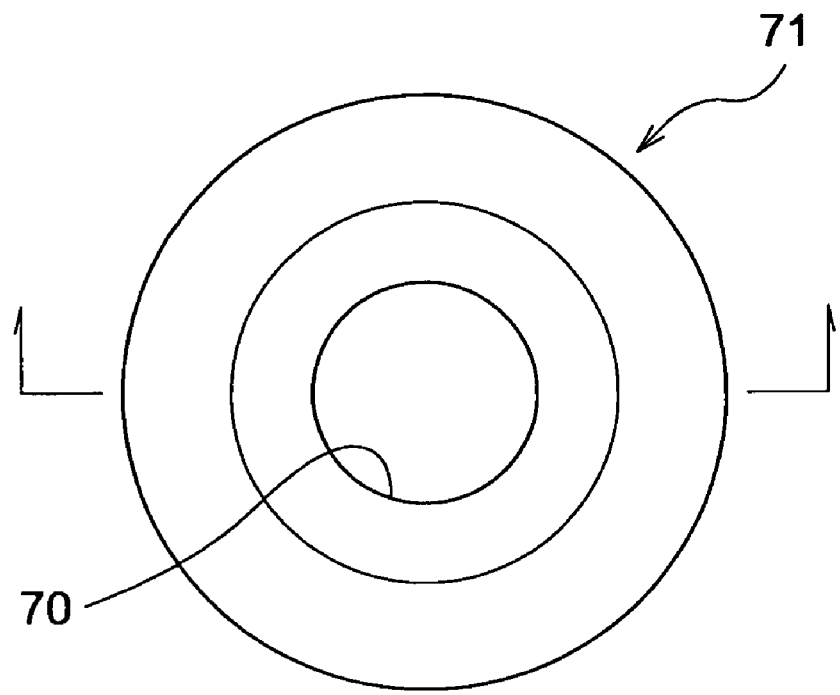
(b)
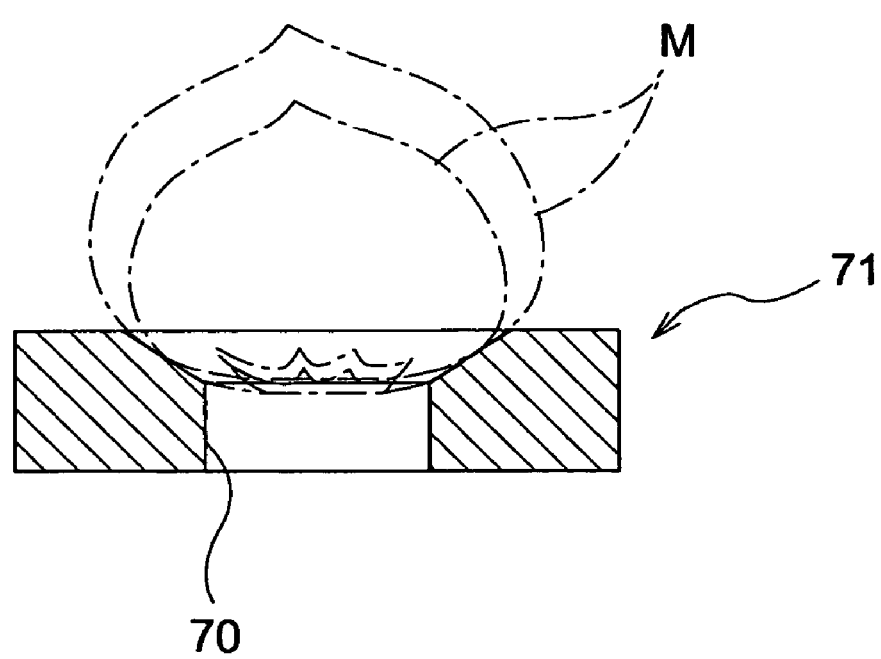

FIG.18
(a)
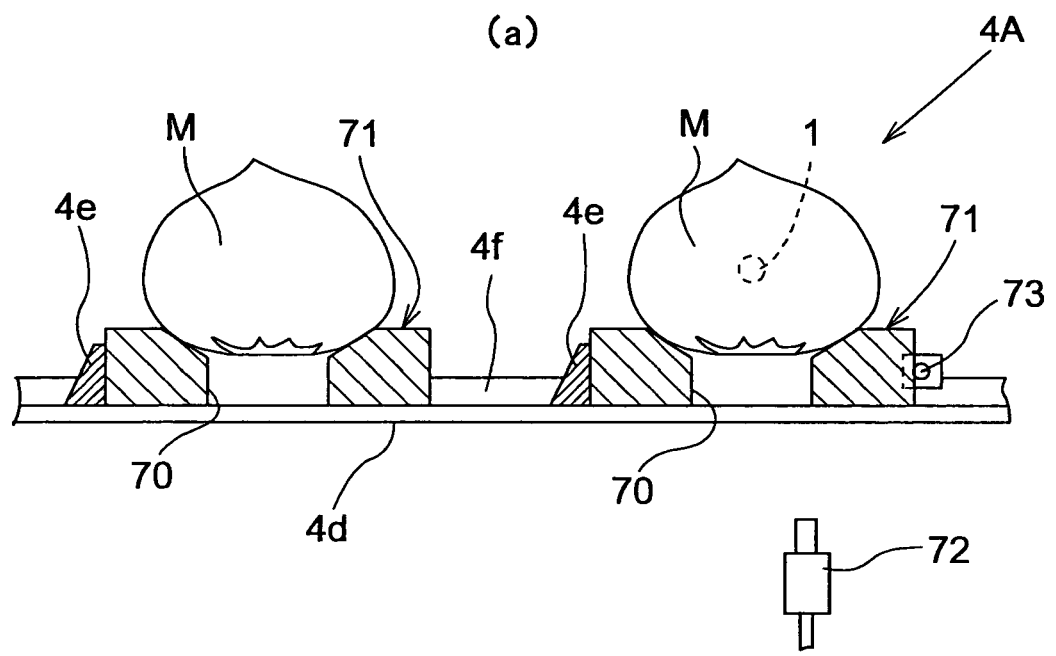
(b)
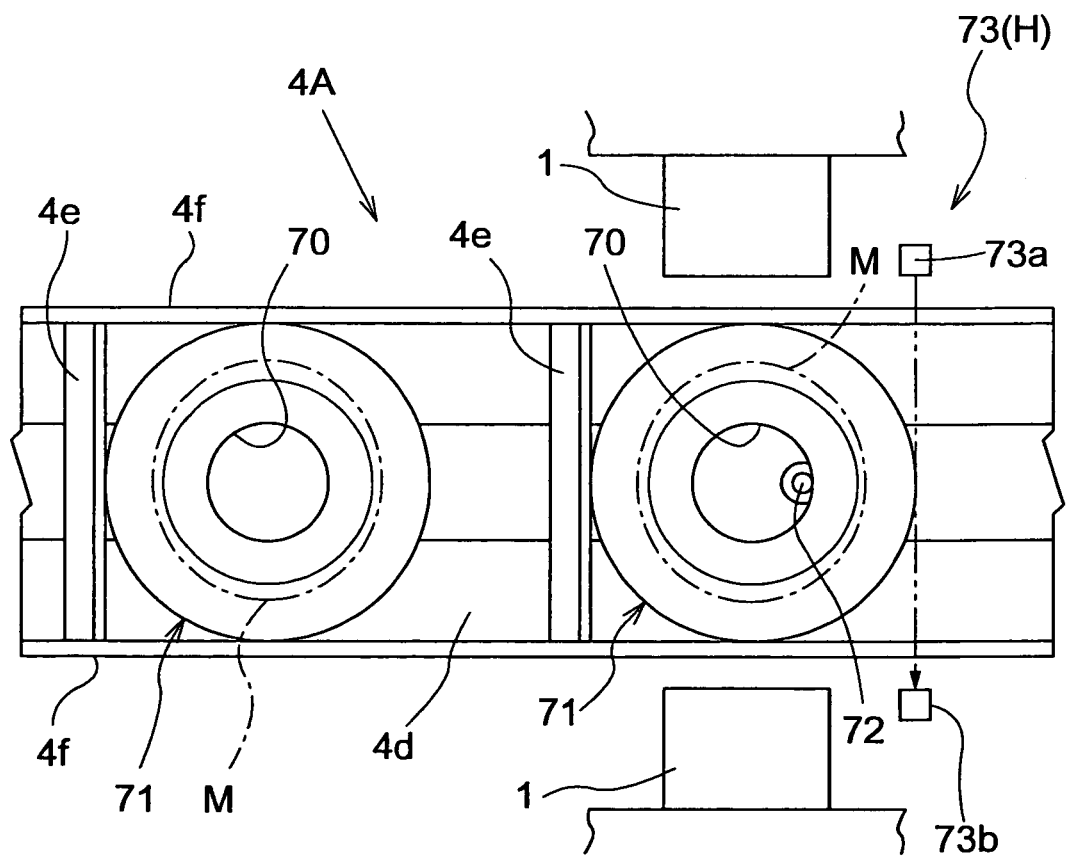

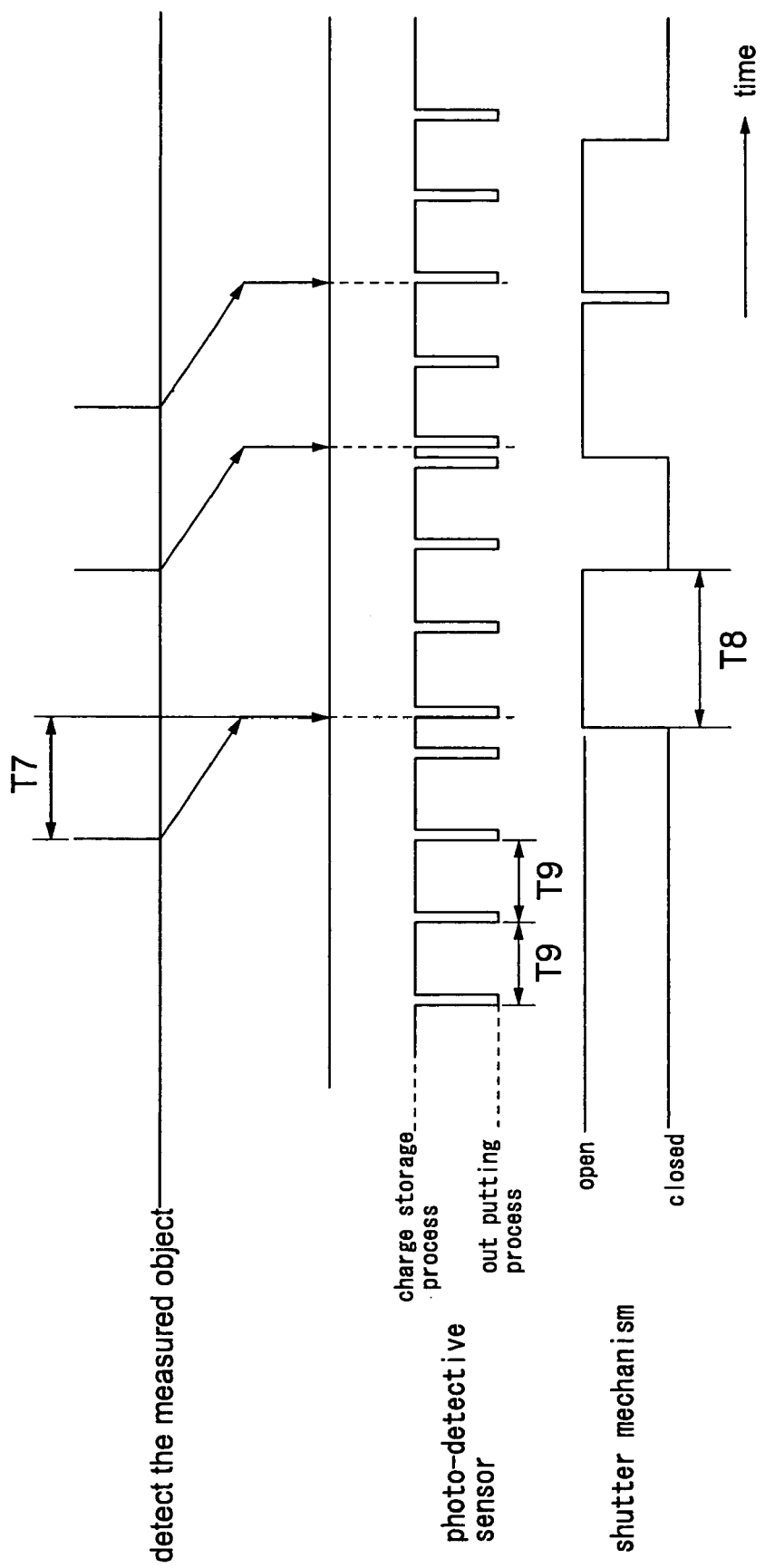

QUALITY EVALUATION APPARATUS FOR FRUITS AND VEGETABLES

BACKGROUND OF THE INVENTION

1. Field of the Invention

The present invention relates to a quality evaluation apparatus for fruits and vegetables comprising a light emitting section for emitting light to fruits or vegetables acting as measured objects placed in a position for measurement, a light receiving section for receiving transmitted light or reflected light from the measured objects at a photo-detective sensor of charge storage type to obtain photo-detective information for quality evaluation, a transporting device for transporting the measured objects via the position for measurement, and a control device for obtaining inner quality information of the measured objects based on the photo-detective information from the light receiving section and for controlling operation of the respective sections.

Further, the present invention relates to the quality evaluation apparatus further comprising a computing section for obtaining a quality evaluation value for fruits or vegetables based on photo-detective information from the light receiving section and a calibration formula established in advance for quality evaluation for fruits and vegetables. This computing section is switchable between a state for executing a quality evaluation process of the measured objects, and a state for executing a wavelength calibration process to determine wavelengths of the light received by the light receiving section based on the photo-detective information when a reference object for wavelength calibration is measured which has a light transmission characteristic with respect to near-infrared light of specific wavelengths.

2. Description of Related Art

The quality evaluation apparatus noted above is for measuring the quality of fruits and vegetables such as oranges and apples as the measured objects, for example, including the inner quality like a sugar content, acid degree or the like, in a non-destructive condition. The conventional apparatus has the following construction.

One example of the conventional apparatus carries out a discharging operation twice for releasing charges stored in the photo-detective sensor when a measured object which is transported by the transporting device reaches a position slightly upstream of the position for measurement in a transporting direction, and more particularly when the forward end in the transporting direction of a measured object reaches a light passage point through which the light emitted from the light emitting section passes toward the light receiving section. In such an apparatus, a measurement charge storage process is executed for storing charges in the photo-detective sensor until a charge storage time as a predetermined measurement time elapses when a measured object reaches the position for measurement after the discharging operation is completed. Here, the stored charges are fetched and used as the photo-detective information for quality evaluation, thereby to obtain the inner quality information of the measured objects. In a condition where the forward end in the transporting direction of a measured object does not reach the light passage point, the photo-detective sensor continuously executes the charge storage process while a shutter mechanism is maintained in a closed state to prevent the light from entering the photo-detective sensor from outside. (See Patent Document 1, for example)

According to the above construction, the discharging operation is carried out prior to the measurement charge storage process when a measured object which is transported by the transporting device reaches the position slightly upstream of the position for measurement in the transporting direction. This prevents residual charges from remaining in the photo-detective sensor as much as possible. The photo-detective sensor receives transmitted light or reflected light from the measured object to store charges. However, part of the stored charges sometimes remain within the photo-detective sensor even after a process for fetching the stored charges. When the transmitted light or reflected light is further received from the measured objects with the residual charges being present, there occur errors in the photo-detective information, which in turn cause errors in the inner quality information of the measured objects based on the photo-detective information of the photo-detective sensor. Thus, the discharging operation is carried out prior to the measurement charge storage process, thereby to prevent the residual charges from remaining as much as possible.

With the above conventional construction, the measurement process can be executed while preventing the residual charges from remaining as much as possible when a plurality of measured objects which are transported by the transporting device successively reach the position for measurement at short time intervals. However, when the time intervals at which the measured objects are transported are irregular and become prolonged for the measured objects to be transported to the position for measurement, there is a risk of increasing the charges to be stored since the photo-detective sensor continuously executes the charge storage process unless the forward ends in the transporting direction of the measured objects reach the light passage point.

As noted above, the shutter mechanism is in the closed state to prevent the light from entering the photo-detective sensor from outside unless the forward ends in the transporting direction of the measured objects reach the light passage point. However, dark currents are generated in the photo-detective sensor in such an aphotic condition. If such dark currents are stored for a long time, stored charges are increased, which could cause saturation.

Further, it is required in the above-noted conventional construction to execute the discharging operation within a short period of time after the forward end in the transporting direction of a measured object reaches the light passage point and before the measurement charge storage process is executed. However, it is difficult to effect the discharging operation satisfactorily when saturation occurs as noted above, and residual charges sometimes remain. If it is attempted to obtain the inner quality information of the measured object based on the detected information from the photo-detective sensor under such a condition, there is a chance of causing errors in the inner quality information.

In another example of the conventional apparatus, near-infrared light is emitted to the measured objects from the light emitting section. The light transmitted through the measured objects is separated into rays by a spectroscopic device such as a concave diffraction grating. Subsequently, a photo-detective section detects the rays with wavelengths in the range of 700 nm through 1000 nm among the separated rays. The photo-detective section comprises a photodetector of the array type including a linear CCD line sensor of 1024 bits, i.e. 1024 unit photodetectors. Spectral data is obtained based on the detected information from the photodetectors and put to a quadratic differentiation to obtain second derivative spectral data. An amount of specific component contained in the measured objects is obtained using the second derivative spectral data and a calibration formula established in advance, thereby to measure the inner quality.

In this apparatus, a wavelength calibration process is executed in the following manner. This process utilizes a calibration filter as a reference object for wavelength calibration which reaches peaks in the amount of transmitted light with a pair of specific wavelengths. The photodetector of the array type receives light transmitted through the calibration filter. With reference to a positional relationship between the pair of specific wavelengths and elements (unit photodetectors) receiving the pair of peak wavelengths, each element (unit photodetector) constituting the photodetector of the array type is related to the wavelength of light received by each element. (See Patent Document 2)

Incidentally, the above calibration formula is individually established in advance for each apparatus based on data obtained from an actual measurement of samples similar to the measured objects prior to a measuring process for the measured objects. Although the prior patent documents do not describe how to establish the calibration formula in detail, it has generally been established as follows.

Tens or hundreds of measured objects are prepared as samples to obtain spectral data for each sample using a quality evaluation apparatus. Further, for each sample, a detection process is executed for accurately detecting amounts of chemical components of the measured objects by a special inspection device based on a destructive analysis, for example, thereby to obtain actual component amounts in the measured objects. Then, the spectral data obtained from each sample as noted above, and more particularly photo-detective data for all the elements of the photo-detective photodetector of the array type is used and compared with the detected results of the actual component amounts while the calibration formula is established for representing a relationship between the spectral data and the amount of the specific components by using the multiple regression analysis technique.

Thus, the photo-detective information is conventionally utilized which is obtained at the plural unit photodetectors with the same resolution in executing the wavelength calibration process and in establishing the calibration formula.

With the above-noted arrangement, since the wavelength resolution used in executing the wavelength calibration process is sufficiently small, it is possible to reduce errors in the wavelength in the photo-detective information measured by each unit photodetector when transmitted light from the measured objects is separated into rays and received at the numerous unit photodetector having undergone the wavelength calibration in order to obtain the quality evaluation values of the measured objects. In other words, it is possible to reduce errors in wavelength for the photo-detective information for obtaining quality evaluation values of fruits and vegetables acting as measured objects.

In the conventional apparatus noted above, the calibration formula is established with the multiple regression analysis technique using the photo-detective data for all the elements of the photodetector of the array type including numerous elements (unit photodetectors) capable of detecting separated rays with a small resolution. However, it is required to execute a great number of calculations when the calibration formula is established using the multiple regression analysis technique. As a result, an enormous working time is disadvantageously required in establishing the calibration formula.

In order to reduce the working time required in establishing the calibration formula, it is conceivable to reduce the number of plural unit photodetectors to diminish the photo-detective information by decreasing the wavelength resolution when separated rays are received. However, such a proposed arrangement would decrease the wavelength resolution per se when separated rays are received at the plurality of unit photodetectors, even if the above-noted wavelength calibration process is properly executed to determine the wavelengths received at the unit photodetectors, respectively, based on the data received at each unit photodetector. As a result, there occurs a risk of lowering the measurement accuracy of the photo-detective information for obtaining the quality evaluation values of fruits and vegetables.

[Patent Document 1]
Japanese Patent Publication No. 2002-107294 (see pages 5 through 6, FIG. 5 and FIG. 6)

[Patent Document 2]
Japanese Patent Publication No. 2002-90301 (see pages 3 through 5, FIG. 1, FIG. 4 and FIG. 5)

SUMMARY OF THE INVENTION

The present invention has been made having regard to the state of the art noted above, and its object is to provide a quality evaluation apparatus for fruits and vegetables capable of preventing errors occurring in the inner quality information of measured objects by obtaining photo-detective information for quality evaluation in an utmost proper condition with residual charges reduced in the photo-detective sensor.

A further object of the present invention is to provide a quality evaluation apparatus capable of reducing the working time for establishing the calibration formula without lowering measurement accuracy when the quality evaluation values for fruits and vegetables are obtained.

A first characteristic of the present invention is as follows.

A quality evaluation apparatus for fruits and vegetables according to the present invention comprises a light emitting section for emitting light to fruits or vegetables acting as measured objects placed in a position for measurement, a light receiving section for receiving transmitted light or reflected light from the measured objects at a photo-detective sensor of charge storage type to obtain photo-detective information for quality evaluation, a transporting device for transporting the measured objects via the position for measurement, and a control device for obtaining inner quality information of the measured objects based on the photo-detective information from the light receiving section and for controlling operation of the respective sections. The control device repeatedly executes a charge storage discharge process for allowing the photo-detective sensor to store charges until a predetermined charge storage time elapses from start of charge storage and then releasing the charges stored in the photo-detective sensor until lapse of a predetermined discharge time when a measured object is not present in the position for measurement or when the photo-detective information for quality evaluation has already been obtained even if a measured object is present in the position for measurement. The control device also allows the photo-detective sensor to release the charges stored therein until the predetermined discharge time elapses when a measured object transported by the transporting device reaches the position for measurement, and then executes a measurement charge storage process for storing charges in the photo-detective sensor to be used as the photo-detective information for quality evaluation until lapse of a predetermined measurement time.

More particularly, the measured objects are transported by the transporting device via the position for measurement. The photo-detective information for quality evaluation is obtained when a measured object is placed in the position for measurement, thereby to obtain the inner quality information of the measured object. The control device repeatedly executes a charge storage discharge process for allowing the photo-detective sensor to store charges until a predetermined charge storage time elapses from start of charge storage and then releasing the charges stored in the photo-detective sensor until lapse of the predetermined discharge time when a measured object is not present in the position for measurement or when the photo-detective information for quality evaluation has already been obtained even if a measured object is present in the position for measurement. In other words, the charge storage discharge process is repeatedly executed whenever the measurement charge storage process is off. Thus, the operation for releasing the stored charges is repeated at predetermined time intervals, thereby to sufficiently release the charges stored in the photo-detective sensor. This results in a reduced chance of the charges remaining in the photo-detective sensor after the operation for releasing the charges is completed.

The control device allows the photo-detective sensor to release the charges stored therein until the predetermined discharge time elapses when a measured object transported by the transporting device reaches the position for measurement, and then executes a measurement charge storage process for storing charges in the photo-detective sensor to be used as the photo-detective information for quality evaluation until lapse of a predetermined measurement time. The charges stored in the measurement charge storage process are used as the photo-detective information for quality evaluation, thereby to obtain the inner quality information of the measured objects.

It should be noted that there is a reduced chance of the charges remaining in the photo-detective sensor after completion of the operation for releasing the charges when the charge storage discharge process is repeatedly executed as noted above. Thus, there is little chance of the charges remaining in the photo-detective sensor after the operation for releasing the charge is completed in the measurement charge storage process, which decreases errors caused by residual charges when the transmitted light or reflected light from the measured objects is received to obtain the photo-detective information.

Thus, the quality evaluation apparatus for fruits and vegetables can be provided which is capable of reducing errors in the inner quality information of the measured objects by obtaining the photo-detective information for quality evaluation in an utmost proper condition with the residual charges reduced in the photo-detective sensor.

A second characteristic of the quality evaluation apparatus for fruits and vegetables according to the present invention lies in further comprising an incidence switching device switchable between an open state for allowing the transmitted light or reflected light from the measured objects to be received at the photo-detective sensor, and a closed state for preventing the light from being received at the photo-detective sensor, in which the control device controls operation of the incidence switching device to switch from the closed state to the open state when a measured object reaches the position for measurement, and to reinstate the closed state after the open state is maintained until lapse of the predetermined measurement time.

More particularly, when a measured object reaches the position for measurement, the incidence switching mechanism is switched from the closed state for preventing the transmitted light or reflected light from being received at the photo-detective sensor to the open state for allowing the transmitted light or reflected light from the measured object to be received at the photo-detective sensor. This establishes the condition in which the transmitted light or the reflected light from the measured object is received at the photo-detective sensor, thereby to properly execute the measurement charge storage process. Then, the switching mechanism is returned to the closed state after being maintained in the open state until lapse of the predetermined measurement time after it is switched to the open state. As a result, the incidence switching mechanism is maintained in the closed state when the measurement charge storage process is not executed.

Therefore, it is possible that the transmitted light or reflected light from the measured object is received at the photo-detective sensor only while the measurement charge storage process is executed to properly execute the measurement charge storage process. In addition, the transmitted light or reflected light from the measured object is not received at the photo-detective sensor when the charge storage discharge process is repeatedly executed, which can prevent the residual charges occurring in the photo-detective sensor.

A third characteristic of the quality evaluation apparatus for fruits and vegetables according to the present invention lies in that the transporting device transports the measured objects as placed in particular positions on saucers, and that the control device includes a saucer detecting device for detecting that a forward end in a transporting direction of a saucer has reached a predetermined position, thereby to determine that a measured object has reached the position for measurement based on detection information from the saucer detecting device.

More particularly, the measured objects are transported as placed as placed in particular positions on the saucers. The apparatus detects the forward end in the transporting direction of a saucer having reached the predetermined position to determine that a measured object has reached the position for measurement based on the detection information from the saucer detecting device when the measured objects are transported as placed on the saucers as note above.

For example, when the positional relationship between the predetermined position and the position for measurement is related to the positional relationship between the forward end of the saucer and the particular position, the apparatus is capable of determining that a measured object has reached the position for measurement immediately when at the saucer detecting device detects that the forward end in the transporting direction of the saucer has reached the predetermined position. Further, it is possible to determine that the measured object has reached the position for measurement upon lapse of time required for the object to be transported to the position for measurement after the saucer detecting device detects that the forward end in the transporting direction of the saucer has reached the predetermined position.

Thus, since the position on the saucer where the measured object is placed is determined, the position relationship between the forward end of the saucer and the measured object is substantially constant regardless of the size of the measured object. In other words, the positional relationship between the forward end of the saucer and the measured object is constant even when the measured object is small. Thus, the position of the measured object is in the constant positional relationship regardless of the size of the object when the saucer detecting device detects that the forward end in the transporting direction of the saucer reaches the predetermined position. Therefore, it is possible to determine that the measured object reaches the position for measurement based on the detection information from the saucer detecting device. Further, it is also possible to properly determine that the measured object has reached the position for measurement even when the object is small.

A fourth characteristic of the quality evaluation apparatus for fruits and vegetables according to the present invention lies in that the control device includes an object detecting device for detecting that a forward end in a transporting direction of a measured object transported by the transporting device has reached a position upstream of the position for measurement in the transporting direction, and a transporting distance measuring device for measuring a transporting distance of the measured objects transported by the transporting device, and that the control device determines that a measured object has reached the position for measurement based on detection information from the transporting distance measuring device after detecting that the forward end of the measured object has reached the upstream position based on detection information from the object detecting device.

More particularly, a measured object is determined to have reached the position for measurement when it is detected that the measured object is transported from the upstream position to the position for measurement based on the detection information from the transporting distance detecting device after it is detected that the forward end of the measured object has reached the upstream position. When it is detected by the object detecting device that the forward end in the transporting direction of the measured object transported by the transporting device has reached the position upstream of the position for measurement in the transporting direction, it is determined based on the detection information from the transporting distance measuring device that the transporting distance of the measured object to move from that point corresponds to the distance from the upstream position to the position for measurement. Based on this, it is determined that the measured object has reached the position for measurement. Thus, it is possible to determine properly that the measured object has reached the position for measurement even when the object is transported without being placed on the saucer.

A fifth characteristic of the quality evaluation apparatus for fruits and vegetables according to the present invention lies in comprising a light emitting section for emitting near-infrared light to measured objects placed in a position for measurement;

a light receiving section for separating the light transmitted through or reflected from the measured objects into rays and receiving the separated rays at a plurality of unit photodetectors; and a computing section for executing a quality evaluation process to obtain quality evaluation values of fruits or vegetables based on photo-detective information from the light receiving section obtained when the fruits or vegetables as the measured objects are measured and on a calibration formula established in advance for quality evaluation of the fruits and vegetables;

the computing section being switchable to a state for executing a wavelength calibration process, instead of the quality evaluation process, to determine wavelengths received by the plurality of unit photodetectors, respectively, based on photo-detective information from the light receiving section obtained when a reference object for wavelength calibration is measured as the measured object which has characteristics in light transmission with respect to the near-infrared light of a specific wavelength;

wherein the calibration formula is established by using the photo-detective information with a resolution greater than a maximum resolution of the photo-detective information determined by the number of the plurality of unit photodetectors, and wherein the computing section executes the wavelength calibration process by using the photo-detective information with a resolution smaller than the resolution with which the calibration formula is established.

More particularly, the calibration formula is established by using the photo-detective information with a resolution greater than a maximum resolution of the photo-detective information determined by the number of plural unit photodetectors. In other words, even when the number of unit photodetectors is increased to reduce the wavelength resolution with which the rays separated from the transmitted light or reflected light from the measured objects are received, the calibration formula is established by using the photo-detective information with a resolution greater than the maximum resolution of the photo-detective information determined by the plurality of unit photodetectors. Thus, when the calibration formula is established by using the multiple regression analysis technique, for example, the number of data in the photo-detective information can be reduced, thereby to minimize the number of calculations to be performed and reduce the working time required for establishing the calibration formula.

Since the wavelength calibration process is executed using the photo-detective information with the resolution smaller than the resolution with which the calibration formula is established, it is possible to determine, with the small resolution, the wavelengths received by the plurality of unit photodetectors, respectively. Thus, the photo-detective information obtained by receiving the light at the plurality of unit photodetectors is obtained with reduced wavelength errors compared with the case where a wavelength calibration process is executed with the same resolution as in establishing the calibration formula. As a result, measurement errors are reduced when the quality evaluation values of fruits and vegetables are obtained.

In addition, the photo-detective information measured in advance for establishing the calibration formula is also obtained with reduced wavelength errors. Therefore, it is possible to establish a proper calibration formula by proper photo-detective information corresponding to the correct wavelengths in spite of the reduced number of data in the photo-detective information.

Thus, it is possible to provide the quality evaluation apparatus for fruits and vegetables capable of reducing the working time and effort required for establishing the calibration formula without lowering the measurement accuracy when the quality evaluation values of fruits and vegetables are obtained.

A sixth characteristic of the quality evaluation apparatus for fruits and vegetables according to the present invention lies in that the computing section executes the wavelength calibration process with the maximum resolution of the photo-detective information.

More particularly, since the wavelength calibration process is executed with the maximum resolution of the photo-detective information, it is possible to execute the wavelength calibration process accurately with the maximum resolution of the photo-detective information obtained by receiving the light at the plural unit photodetectors for determining the wavelengths received by the plural unit photodetectors, respectively. In other words, the wavelength calibration process can be executed with the high resolution similar to the wavelength resolution with which the light is received at the plural unit photodetectors. Thus, it is possible to relate the respective unit photodetectors to the received wavelengths with reduced errors after the wavelength calibration process is executed.

A seventh characteristic of the quality evaluation apparatus for fruits and vegetables according to the present invention lies in that the reference object for wavelength calibration has two or more specific wavelengths as the specific wavelength, and that the computing section determines a plurality of unit photodetectors receiving the plurality of specific wavelengths among the plurality of unit photodetectors in the wavelength calibration process, thereby to obtain the wavelengths received by the other unit photodetectors based on position information of the particular unit photodetectors with respect to all the unit photodetectors and the specific wavelengths.

More particularly, the reference object having two or more specific wavelengths as the specific wavelength is used as the reference object for wavelength calibration in executing the wavelength calibration process. The near-infrared light is emitted from the light emitting section to the reference object to separate the transmitted light or reflected light from the reference object into rays which are received at the plural unit photodetectors. The reference object has characteristics in light transmission with specific wavelengths. The unit photodetectors corresponding to the specific wavelength among the plural unit photodetectors are in different photo-detective conditions to the other units, thereby to determine the unit photodetectors receiving the plurality of specific wavelengths.

Thus, based on the position information of the plural unit photodetectors determined as noted above and the plurality of specific wavelengths, respectively, it is possible to obtain a corresponding relationship between the position information from the unit photodetectors other than the particular unit photodetectors and the wavelengths received by these photodetectors, thereby to execute the wavelength calibration process.

An eighth characteristic of the quality evaluation apparatus for fruits and vegetables according to the present invention lies in that the light receiving section receives light of a predetermined wavelength band including the specific wavelengths at 1024 unit photodetectors, wherein the computing section determines the wavelengths of the separated rays with a wavelength resolution of 0.8 nanometers or less in executing the wavelength calibration process, and determines the wavelengths of the separated rays with a wavelength resolution of 2 nanometers or more to obtain the quality evaluation values of the measured objects in establishing the calibration formula.

More particularly, since the light of the predetermined wavelength band including the specific wavelengths is received at the numerous, 1024 unit photodetectors, the light of the specific wavelength band is received with high resolution. Where, for example, oranges or apples are the measured objects, the predetermined wavelength band is generally from several hundred nanometers to a thousand nanometers. Thus, the separated rays are received with a sufficiently high resolution. If the light is received with a higher resolution in order to increase the measurement accuracy, the amount of light received at the unit photodetectors can be insufficient. On the other hand, if a large amount of light is emitted from the light emitting section in order to secure a sufficient light amount, the fruits or vegetables may be damaged.

Since the wavelength resolution is set to 0.8 nanometers or less for determining the wavelengths of the separated rays in order for the computing section to execute the wavelength calibration process, the quality evaluation values of fruits and vegetables can be obtained accurately with less errors than the measurement errors generally required.

To describe this aspect with reference to actual measured data obtained by the applicant, FIG. 15 shows results representing a relationship between amounts of wavelength error when the specific wavelength deviates from a proper value and variations in obtained sugar content, in obtaining the sugar content of apples as the quality evaluation value of fruits and vegetables. Specifically, when wavelength errors occur as represented by the horizontal axis, the required sugar content has different values. In the case of fruit such as apples, measurement errors of 0.5 degrees or less are generally required. As apparent from FIG. 15, the wavelength errors of 0.8 nanometers or less will satisfy the required measurement accuracy of 0.5 degrees or less.

Since the wavelength resolution is set to 0.8 nanometers or less with which the wavelengths of the separated rays are determined in order to execute the wavelength calibration process as described above, the generally required measurement accuracy as noted above can be achieved.

Since the wavelength resolution is set to 2 nanometers or more with which the wavelengths of the separated rays are determined in order to obtain the quality evaluation values of the measured objects in establishing the calibration formula, the calibration formula is established by calculation process using the multiple regression analysis technique, for example, utilizing the photo-detective information of the unit photodetectors less than 1024 obtained at wavelength intervals of 2 nanometers or more among the 1024 unit photodetectors.

Therefore, the number of data in the photo-detective information is reduced in establishing the calibration formula to minimize the number of calculations, thereby to reduce the working time and effort in establishing the calibration formula.

A ninth characteristic of the quality evaluation apparatus for fruits and vegetables according to the present invention lies in further comprising a light amount adjusting device for varying and adjusting a light amount of light received by the light receiving section in the transmitted light or reflected light from the measured object.

More particularly, since the light amount adjusting device is operable to vary and adjust the amount of light received by the light receiving section of the transmitted light or reflected light from the measured objects, it is possible to adjust the light amount incident on the light receiving section when a large amount of light is emitted from the measured object. Thus, the light amount incident on the light receiving section can be adjusted to a proper amount.

Further, even when any other light is present than the transmitted light or reflected light from the measured objects between the measured objects and the plurality of unit photodetectors, such light other than the transmitted light or reflected light is adjusted by the light amount adjusting device to enter the light receiving section, thereby to prevent a reduction in S/N (signal to noise) ratio.

A tenth characteristic of the quality evaluation apparatus for fruits and vegetables according to the present invention lies in further comprising a horizontal position adjusting device for varying and adjusting a light emitting position of the light emitting section and a light receiving position of the light receiving section relative to the position for measurement, respectively, along a direction in which these positions move toward or away from each other.

More particularly, since the horizontal position adjusting device is operable to vary and adjust a light emitting position of the light emitting section and a light receiving position of the light receiving section relative to the position for measurement, respectively, along the direction in which these positions move toward or away from each other, the light emitting position can be moved closer to or away from the measured objects placed in the position for measurement. Therefore, light can be emitted effectively to the measured objects by focusing the emitting light on or adjacent surfaces of the measured objects, for example. Similarly to the case of the light emitting position, the light receiving position can be moved closer to or away from the measured objects placed in the position for measurement, which allows the light transmitted through the measured objects to be effectively received by setting a light-receiving focal position to or adjacent the surfaces of the measured objects.

An eleventh characteristic of the quality evaluation apparatus for fruits and vegetables according to the present invention lies in further comprising an incidence switching device switchable between an open state for allowing the transmitted light or reflected light from the measured objects to be received at the unit photodetectors, and a closed state for preventing the transmitted light or reflected light from the measured objects from being received at the unit photodetectors; and an operation control device for controlling operation of the respective sections;

wherein the operation control device controls operation of the incidence switching device to switch from the closed state to the open state when the measured objects are placed in the position for measurement, and to reinstate the close stated after the open state is maintained until lapse of an open state maintaining time, and controls operation of the light receiving section to execute a measurement process for receiving the light from the measured objects at the unit photodetectors while the incidence switching device is maintained in the open state.

More particularly, the operation control device controls the operation of the incidence switching device to switch the incidence switching device from the closed state to the open state when a measured object is placed in the position for measurement, and to reinstate the close stated after the open state is maintained until lapse of an open state maintaining time. In the closed state, the transmitted light or reflected light from the measured objects is not received at the unit photodetectors. On the other hand, in the open state, the transmitted light or reflected light from the measured objects is received at the unit photodetectors whereby the measurement process is executed.

Therefore, in a condition in which no measured object is present in the position for measurement, the light emitted from the light emitting section is not directly received at the unit photodetectors, which allows the transmitted light or reflected light from the measured objects to be properly received.

A twelfth characteristic of the quality evaluation apparatus for fruits and vegetables according to the present invention lies in further comprising a transporting device for transporting the measured objects via the position for measurement.

More particularly, since the measured objects are transported via the position for measurement by the transporting device, it is possible to execute the measurement process effectively by transporting the measured objects successively with the transporting device even when a large number of objects are measured. Even when the measured objects are classified into a plurality of grades according to the measurement results of the quality evaluation values, it is possible to transport the objects to a position for sorting.

A thirteenth characteristic of the quality evaluation apparatus for fruits and vegetables according to the present invention lies in further comprising a shading device for blocking stray light entering the unit photodetectors without being transmitted through the measured objects, in the light emitted from the light emitting section, while allowing the measured objects transported by the transporting device to pass through the position for measurement.

More particularly, by providing the shading device, it is possible to effectively block stray light entering the plurality of unit photodetectors without being transmitted through the measured objects, out of the light emitted from the light emitting section. As a result, there is a reduced chance of the light erroneously detected at the plurality of unit photodetectors. Moreover, the shading device can effectively block stray light while allowing the measured objects transported by the transporting device to pass through the position for measurement. Thus, the transportation by the transporting device is not hampered, and thus little possibility of lowering the working efficiency.

BRIEF DESCRIPTION OF THE DRAWINGS

FIG. 14 is a graph showing a relationship between wavelength and light amount;
FIG. 17 is a view showing saucers according to the modified embodiment;
FIG. 18 is a view showing a condition in which measured objects are detected according to the modified embodiment.

FIG. 26 is a timing chart of measurement operation according to a still further modified embodiment.

DESCRIPTION OF THE PREFERRED EMBODIMENTS

Embodiments of the present invention will be described hereinafter with reference to the accompanying drawings.

First Embodiment

A first embodiment of a quality evaluation apparatus for fruits and vegetables according to the present invention will be described below with reference to the drawings.

The quality evaluation apparatus for fruits and vegetables according to the present invention is an apparatus for measuring sugar contents or acid degrees as quality of fruits and vegetables such as oranges which are one example of measured objects. This apparatus comprises a light emitting section for emitting light to fruits or vegetables to be measured and placed in a position for measurement, a light receiving section for receiving transmitted light from the objects at a photo-detective sensor of the charge storage type to obtain photo-detective information for quality evaluation, a transporting device for transporting the measured objects via the position for measurement, and a control device for obtaining inner quality information on the objects based on the photo-detective information from the light receiving section and for controlling operations of the respective sections.

Figure 1:
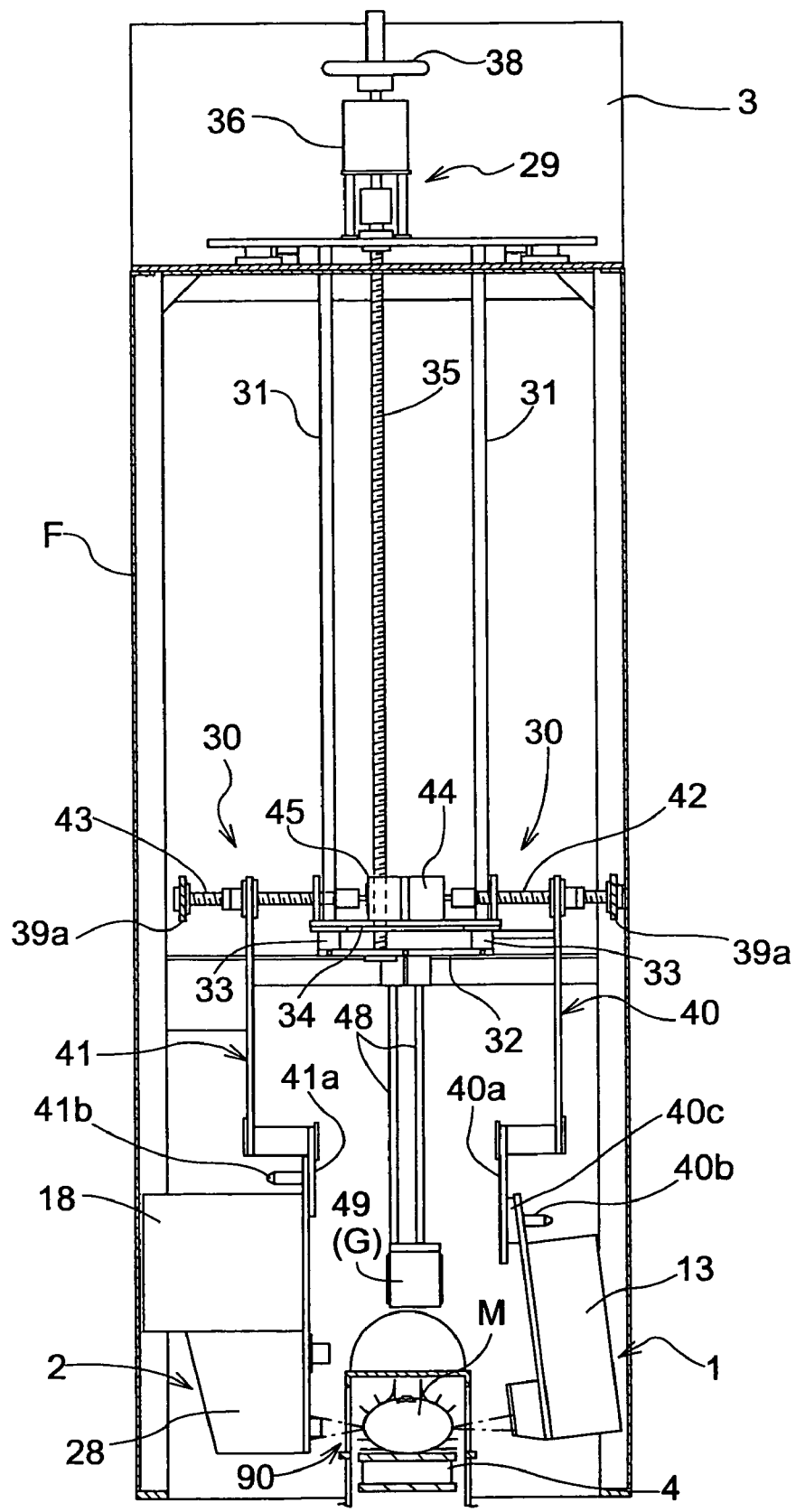
FIG. 1 is a front view of a quality evaluation apparatus.
Figure 2:
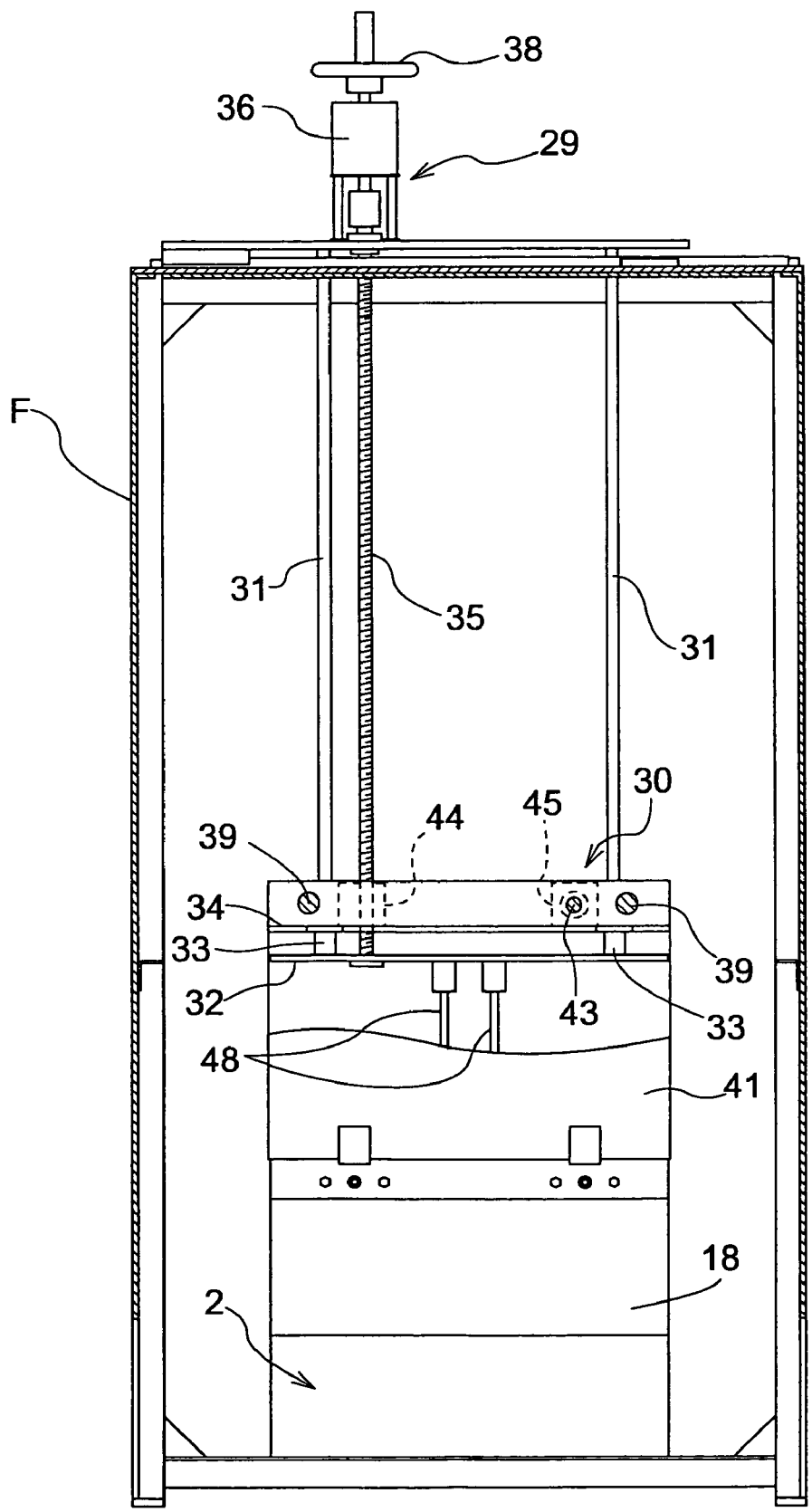
FIG. 2 is a side view of the quality evaluation apparatus.

Specifically, as shown in FIG. 1, the quality evaluation apparatus comprises a light emitting section 1 for emitting light to measured objects M, a light receiving section 2 for receiving light transmitted through the objects M to measure the light received, and a control section 3 utilizing a micro computer to execute various control processes. The measured objects M are lined up in tandem on and transported by a transport conveyor 4 acting as the transporting device to pass successively through the position for measurement of the apparatus. The light emitted from the light emitting section 1 to the objects M placed in the position for measurement is transmitted through the objects M and received by the light receiving section 2. The light emitting section 1 and the light receiving section 2 are distributed to opposite sides of the position for measurement, or opposite sides in the direction of width of the transport conveyor 4.

(Light Emitting Section)

The light emitting section 1 includes two light sources to emit the light from these two light sources, with light-emitting optical axes different to each other, to a measured object placed in the position for measurement. The two light-emitting optical axes extending from the respective light sources cross each other on or adjacent a surface of the measured object placed in the position for measurement.

Figure 4:
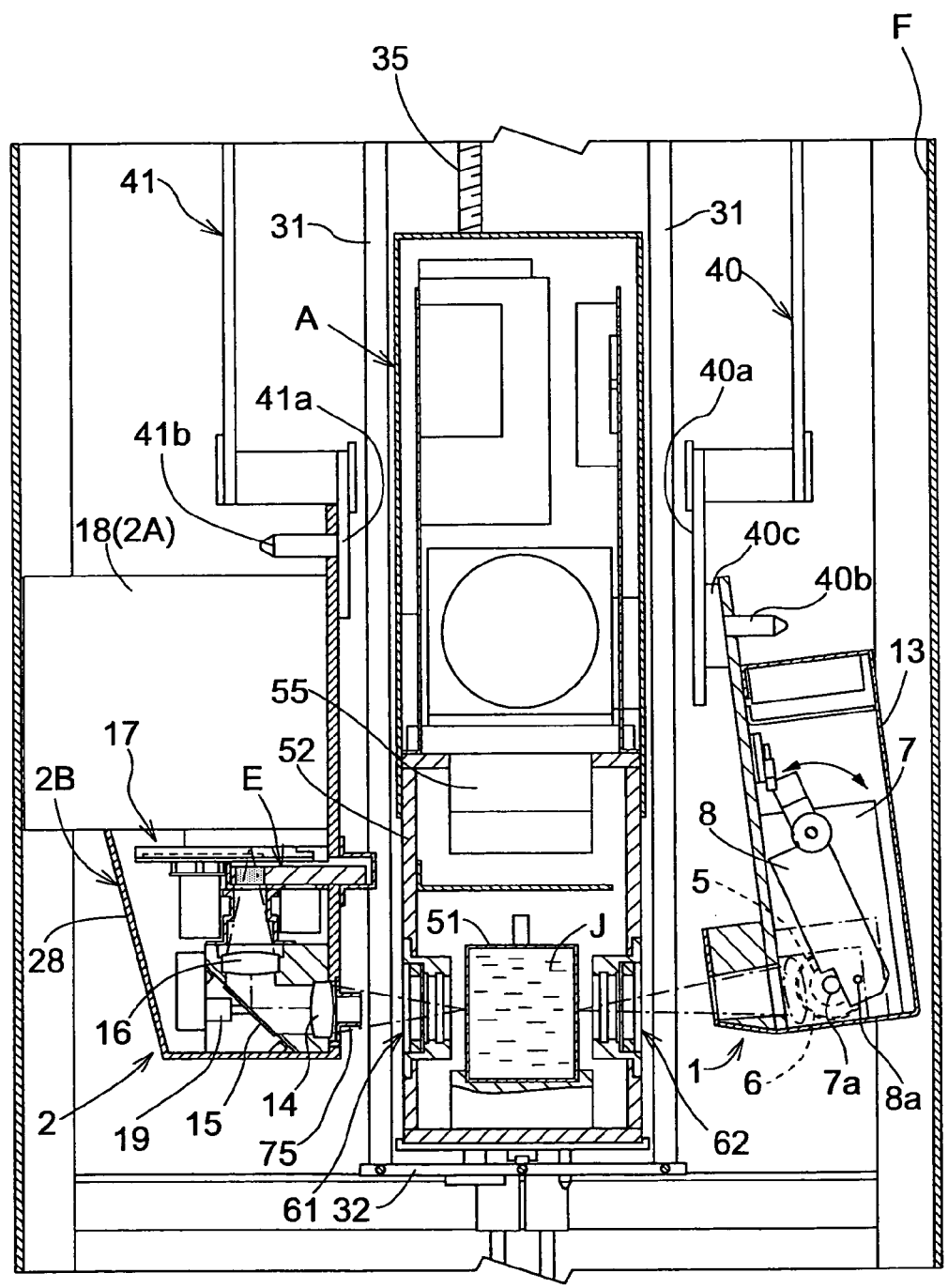
FIG. 4 is a partly cut away front view of the quality evaluation apparatus.
Figure 8:
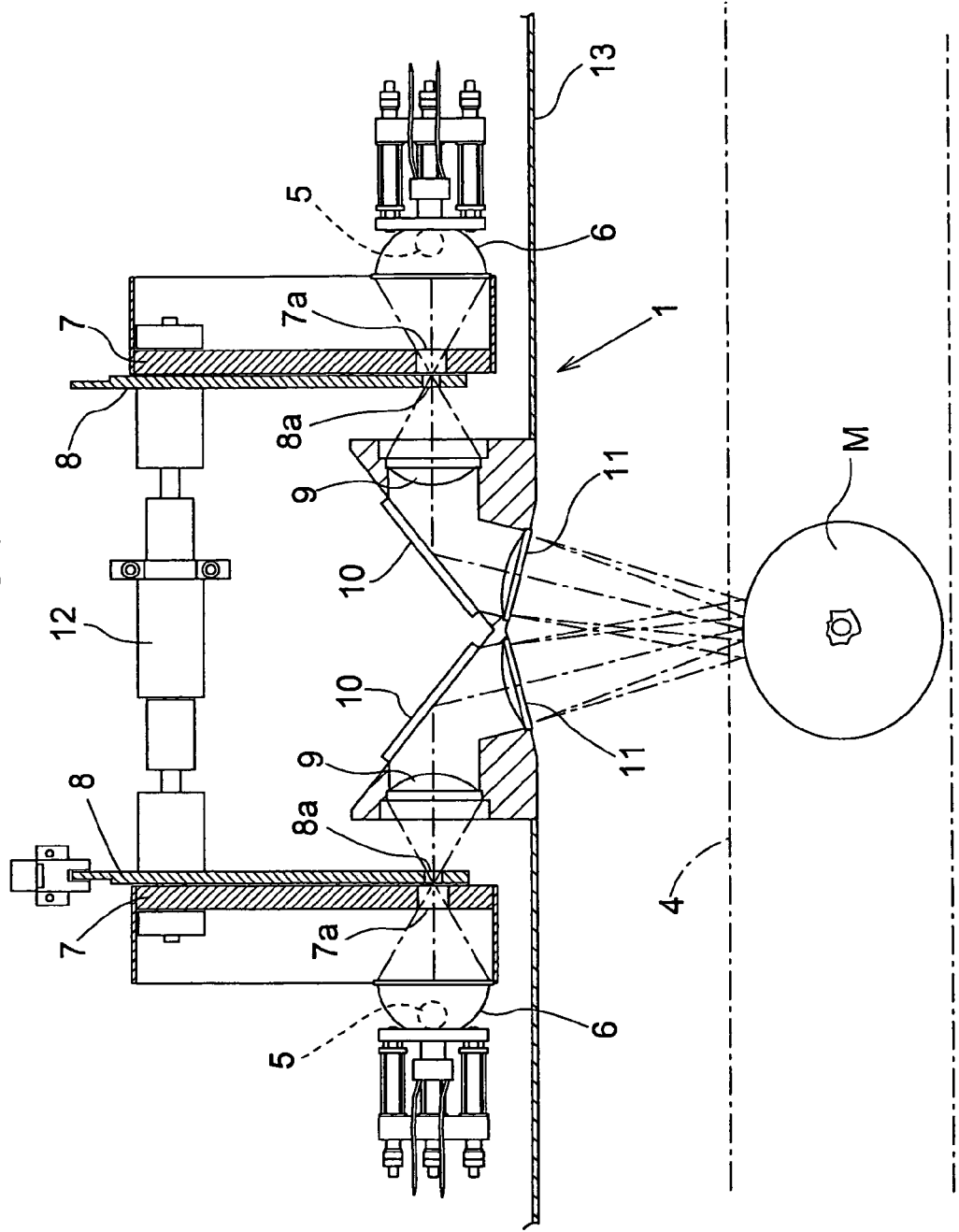
FIG. 8 is a cut away plan view of a light emitting section.

As shown in FIGS. 4 and 8, the light emitting section 1 includes light sources 5 consisting of two halogen lamps spaced apart from each other along a transporting direction of the transport conveyor 4. An optical system as described below is provided corresponding to each of the two light sources 5. First, a light reflector 6 having a concaved shape is provided to act as a condensing device for reflecting the light from the light source 5 and focusing it on the surface of the object M. A diaphragm 7 having a large aperture 7a is disposed adjacent a focal point of the light converged by the light reflector 6. The converged light is restrained from spreading radially outwardly by passing through the large aperture 7a. The optical system corresponding to each light source 5 further comprises a light amount adjusting plate 8 switchable between a state for allowing passage of the light having passed through the diaphragm 7, a state for allowing the light to pass through a small aperture 8a, and a state for blocking the light, a collimator lens 9 for converting the converged light from the light source 5 to parallel light, a reflector 10 for reflecting and deflecting the converted parallel light, and a condenser lens 11 for condensing the light reflected by the reflector 10. The respective light amount adjusting plates 8 are pivotable in unison through a light amount adjusting motor 12 to switch to the above-described states.

The light emitting section 1 includes the above-noted components housed in a casing 13 to form a unit. The light emitting section 1 is provided in a slanting posture to emit light obliquely downward to the measured object in the position for measurement so that the light may not directly enter the light receiving section 2 even when the measured object has a small outer dimension.

(Light Receiving Section)

As shown in FIG. 4, the light receiving section 2 includes a condenser lens 14 for condensing the light transmitted through the measured object M, a band-pass mirror 15 for upwardly reflecting only light in a wavelength range of 680 through 990 nanometers (nm) which is a near-infrared range, out of the converted parallel light, and for allowing light of other wavelengths to pass straight through, a condenser lens 16 for condensing the light to be measured reflected upward by the band-pass mirror 15, a shutter mechanism 17 acting as an incidence switching device to be switchable between an open state for allowing the light having passed through the condenser lens 16 to pass through as it is to be received at the photo-detective sensor and a closed state for preventing the light from being received, a spectroscope 18 for separating the light having passed through the shutter mechanism 17 in the open state into rays to measure spectral data, and a light amount detecting sensor 19 for detecting an amount of the light having passed straight through the band-pass mirror 15.

(Filter Switching Mechanism)

A filter switching mechanism E is provided below the shutter mechanism 17 or upstream thereof in a light incidence direction for switching a plurality of various, light amount adjusting filters to act on the light entering the spectroscope 18.

Figure 13:
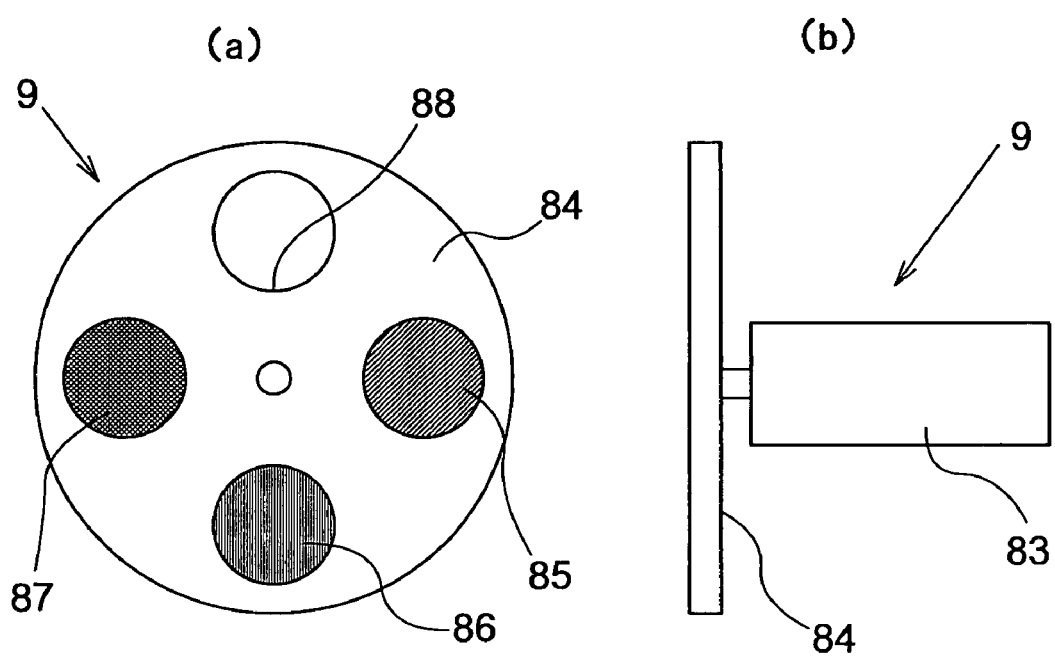
FIG. 13 is a view showing a filter switching mechanism.

As shown in FIG. 13, the filter switching mechanism E comprises a rotary member 84 rotatable by a filter switching motor 83. The rotary member 84 has three filters 85, 86 and 87 and one aperture 88 arranged at intervals circumferentially of the rotary member in positions substantially equidistant from the center of the rotary member 84. The rotary member 84 is rotatable to switch the filters such that either one of the filters may be positioned where the incident light passes.

The first filter 85 is an ND filter having a low optical attenuation ratio, the second filter 86 is an ND filter having a high optical attenuation ratio, and the third filter 87 is a wavelength calibrating filter. More particularly, the rotary member 84 is rotated by driving the filter switching motor 83, thereby to allow the light transmitted from the measured object M to pass through the aperture 88 and enter the spectroscope without attenuation. It is possible to switch between a state in which the light is allowed to enter with little attenuation by passing through the first filter 85 and a state in which the light is allowed to enter with more attenuation by passing through the second filter 86. In other words, it is possible to vary and adjust the amount of the light received by the spectroscope based on measuring conditions (such as the kind, size, transmission factor and the like of the measured objects M, for example) inputted in advance. Thus, a light amount adjusting system is provided by utilizing the filter switching mechanism E. The third filter 87 (wavelength calibrating filter) is used for executing a wavelength calibrating process described hereinafter.

Figure 6:
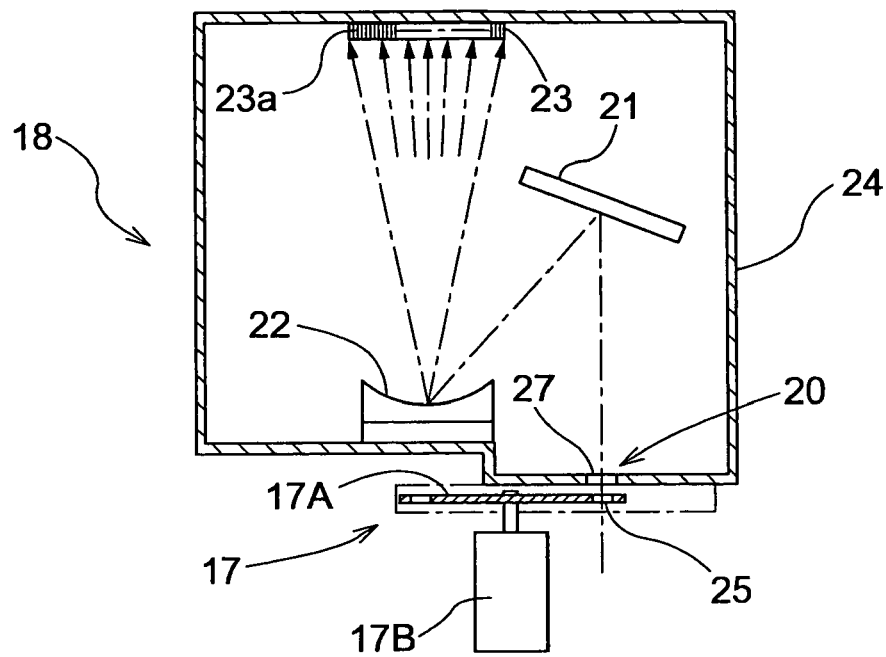
FIG. 6 is a structural view of a spectroscope.

As shown in FIG. 6, the spectroscope 18 includes a reflecting mirror 21 for reflecting the light to be measured which has entered through a light inlet 20 defining a light receiving position, a concave diffraction grating 22 acting as a spectroscopic device for separating the reflected light to be measured into rays of plural wavelengths, and a photo-detective sensor 23 for measuring the spectral data by detecting the amount in each wavelength of the light to be measured separated by the concave diffraction grating 22. These components are arranged in a darkened enclosure 24 made of a shielding material for shielding off external light. The photo-detective sensor 23 is in the form of a CCD line sensor of the charge storage type. The CCD line sensor includes 1024 unit photo-detectors 23a for simultaneously receiving the rays separated and reflected by the concave diffraction grating 22 in a plurality of wavelengths to convert them to signals based on the respective wavelengths for output. The line sensor is formed on a semiconductor substrate. Mounted on the semiconductor substrate are a photoelectric converter for converting a light amount to an electric signal (charge) for each unit photo-detector, a charge storage portion for storing the charges obtained from the photoelectric converter, and a drive circuit for outputting the stored charges to the outside. A thermoelectric cooling device such as a Peltier element, for example, is attached to the back surface of the semiconductor substrate for allowing cooling down to minus 10° C. such that a temperature drift caused by a temperature increase may be avoided thereby to reduce measurement errors due to variations in temperature.

Figure 7:
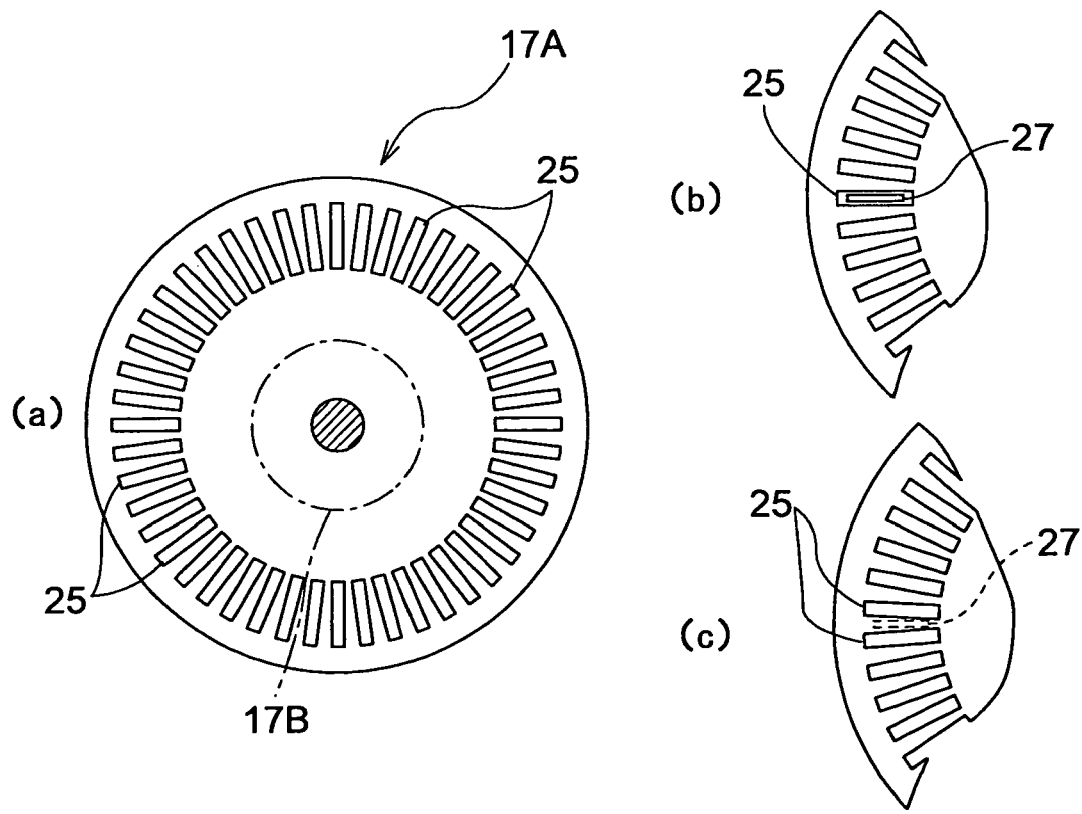
FIG. 7 is a view of a shutter mechanism.

As shown in FIGS. 6 and 7, the shutter mechanism 17 includes a disk plate 17A having a plurality slits 25 radially formed therein, and a pulse motor 17B for rotating the disk plate 17A about a vertical axis. The light inlet 20 of the darkened enclosure 24 has a transmitting slit 27 formed therein which has substantially the same shape as the slits 25. The open state is established as one of the slits 25 vertically registers with the transmitting slit 27 to allow the light to pass therethrough, while the closed state is established as they are displaced from each other thereby to block the light. The disk plate 17A is slidable in tight contact with the light inlet 20 of the darkened enclosure 24 for preventing leakage of the light. In other words, the shutter mechanism 17 is mounted in close proximity to the light inlet 20 to the concave diffraction grating 22. Similarly to the light emitting section 1, the light receiving section 2 includes the above-noted components housed in a casing 28 to form a unit as well.

The light emitting section 1 and the light receiving section 2 are formed as units, respectively, to be mountable in and removable from a light emitting position and a light receiving position, respectively. The light emitting section 1 and the light receiving section 2 are removably mounted on an apparatus frame F. The apparatus frame F includes a pair of attaching portions for the light emitting section 1 and the light receiving section 2 such that positions corresponding to the laterally opposite sides of the transport conveyor 4 across the position for measurement may act as the light emitting position and the light receiving position, respectively.

The apparatus frame F includes a vertical position adjusting mechanism 29 acting as a vertical position adjusting device for vertically adjusting the positions of the light emitting section 1 and the light receiving section 2 in unison. The apparatus frame F further includes a horizontal position adjusting mechanism 30 acting as a horizontal position adjusting device for adjusting the positions of the light emitting section 1 and the light receiving section 2, respectively, along a direction in which each section moves toward and away from the measured object, namely along a horizontal direction perpendicular to the transporting direction of the transport conveyor 4.

(Vertical Position Adjusting Mechanism)

As shown in FIGS. 1 through 5, the vertical position adjusting mechanism is mounted on the apparatus frame F assembled in the form of a rectangular frame to surround outer peripheries of the quality evaluation apparatus. Four fixed support rods 31 are suspended from upper positions of the apparatus frame F. A support table 32 is attached to lower ends of the four fixed support rods 31. A measured member A to be described hereinafter is placed on the support table 32 for calibrating the quality evaluation apparatus. The four fixed support rods 31 include vertically slidable support members 33, respectively, which support a lift deck 34. A feed screw 35 is supported and suspended from an upper position of the apparatus frame F to be rotatable by an electric motor 36. The lift deck 34 has a female screw 37 meshed with the feed screw 35. The feed screw 35 is rotatable by the electric motor 36 thereby to adjust the lift deck 34 to a selected vertical position. The feed screw 35 may be rotated also by a manually operable handle 38.

The lift deck 34 defines a through aperture 34a formed therein to allow the measured member A for calibrating the quality evaluation apparatus placed on the support table 32 to pass vertically therethrough.

(Horizontal Position Adjusting Mechanism)

Figure 5:
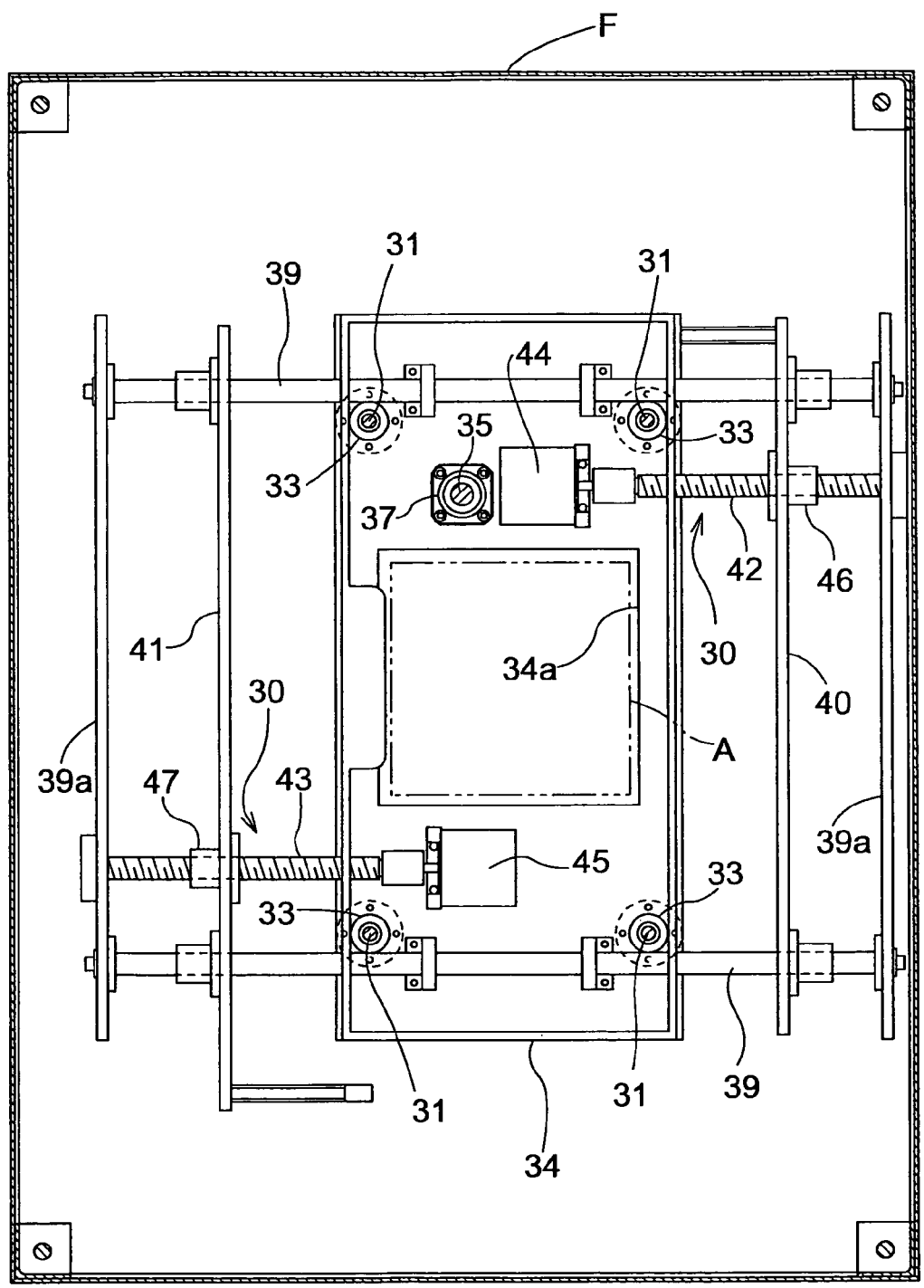
FIG. 5 is a plan view of the quality evaluation apparatus.

As shown in FIG. 5, two guide rods 39 are provided on the lift deck 34 to extend along the direction of arrangement of the light emitting section 1 and light receiving section 2. The guide rods 39 include support members 40 and 41 slidably supported thereon to act as the pair of attaching portions for removably mounting the light emitting section 1 and light receiving section 2 assembled as units, respectively. The guide rods 39 are connected to each other at longitudinally opposite ends thereof through connecting members 39a. The lift deck 34 includes two feed screws 42 and 43 extending in the direction of arrangement of the light emitting section 1 and light receiving section 2 to be rotatable by electric motors 44 and 45, respectively. The support members 40 and 41 have female screws 46 and 47 meshed with the feed screws 42 and 43, respectively. The feed screws 42 and 43 are rotatable in a forward or backward direction by the electric motors 44 and 45 independently, thereby to adjust the positions of the support members 40 and 41, respectively, along the horizontal direction perpendicular to the transporting direction of the transport conveyor 4. Thus, the positions of the light emitting section 1 and light receiving section 2 are adjustable relative to the position for measurement in the horizontal direction, namely in the direction along which the sections move toward or away from the position for measurement by rotating the feed screws 42 and 43 in the forward or backward direction, respectively, by the electric motors 44 and 45.

As described above, the lift deck 34 is vertically adjustable by rotating the feed screw 35 by the electric motor 36, as a result of which the light emitting section 1 and light receiving section 2 supported by the lift deck 34 are vertically moved in unison. On the other hand, the electric motors 44 and 45 are rotatable to adjust the positions of the light emitting section 1 and light receiving section 2, respectively, in the horizontal direction perpendicular to the transporting direction of the transport conveyor 4.

A mounting structure of the light emitting section 1 and light receiving section 2 relative to the support members 40 and 41 will be described next. The support members 40 and 41 have mounting seats 40*a* and 41*a* at lower ends thereof with a plurality of positioning projections 40*b* and 41*b* spaced appropriately in the horizontal direction to project sideways. The light emitting section 1 and light receiving section 2 formed as units have positioning bores corresponding to the positioning projections 40*b* and 41*b*, respectively. As shown in FIGS. 5 and 6, with the positioning projections 40*b* and 41*b* being fitted to the positioning bores, the light emitting section 1 and light receiving section 2 are mounted as bolted in appropriate positions adjacent the projections and bores. When the light emitting section 1 and light receiving section 2 are mounted, the light emitting location where the light emitting section 1 is positioned, the position for measurement, and the light receiving location where the light receiving section 2 is positioned are aligned. It should be noted that the right and left mounting seats 40*a* and 41*a* provided at the lower ends of the support members 40 and 41 have slightly different lengths to each other to correspond to the vertical lengths of the light emitting section 1 and light receiving section 2. The position where the light emitting section 1 is attached includes an inclining position limiting element 40*c* for causing the light to be emitted slightly obliquely downward.

A reference filter 49 is provided above the position for measurement. The reference filter 49 is supported by supporting arms 48 extending downward from the support table 32. The reference filter 49 comprises an optical filter consisting of a pair of opal glass members having predetermined light absorbance characteristics, for example.

Figure 3:
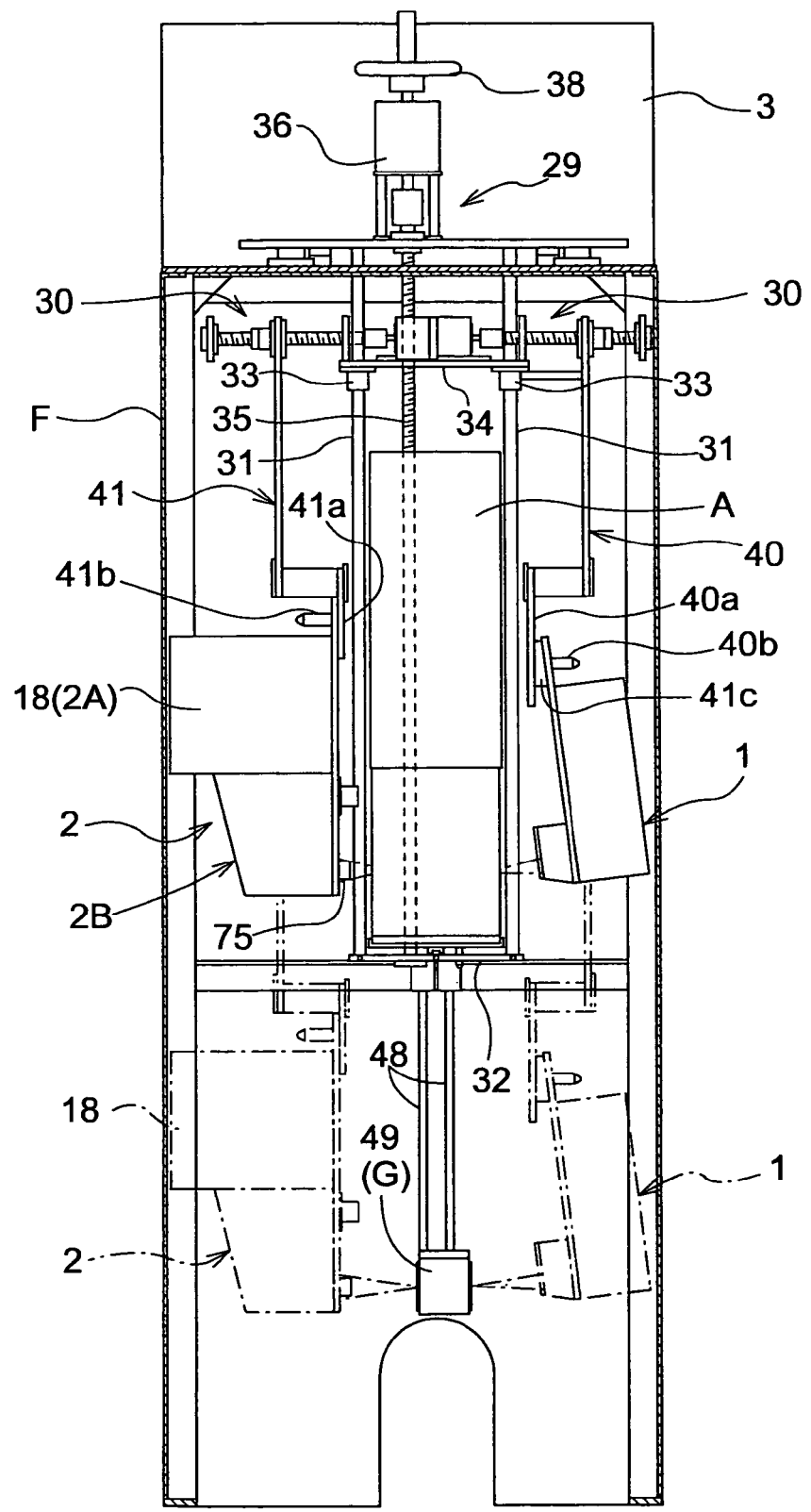
FIG. 3 is a front view of the quality evaluation apparatus.

As shown in FIG. 1, the light emitting section 1 and light receiving section 2 are vertically movable and adjustable in unison by the vertical position adjusting mechanism 29 thereby to be switchable between a normal measuring state where the light from the light emitting section 1 is received by the light receiving section 2 after being transmitted through the measured object M placed on the transport conveyor 4, a reference measuring state as shown in phantom lines in FIG. 3 where the light from the light emitting section 1 is received by the light receiving section 2 after being transmitted through the reference filter 49, and a calibration measuring state as shown in solid lines in FIG. 4.

The outer peripheries of the quality evaluation apparatus are surrounded by walls of the apparatus frame F except for positions through which the measured objects are transported, to prevent entry of external light.

In the quality evaluation apparatus, it is possible to attach and detach the measured member A to/from the support table 32, the measured member having substantially the same characteristics as the light transmission characteristics of the measured objects. The measured member A may be placed on the support table 32 as positionally adjusted, which facilitates attachment and detachment thereof. The measured member A can be removed from the support table 32 when a calibration is not performed.

The measured member A for calibrating the quality evaluation apparatus will be described next. As shown in FIG. 4, outer peripheries of the measured member A are covered by an outer casing 52 having a substantially quadrangular prism shape and made of an opaque member. A container 51 is provided in a lower position of the interior of the outer casing 52 for containing pure water J in a sealed condition to act as an object to be evaluated. An air layer is formed between the container 51 and the outer casing 52. A Peltier element 55 acts on the air layer in order to maintain the temperature of the air layer at the temperature of the measured objects when their quality is evaluated by the quality evaluation apparatus or a predetermined temperature close thereto (e.g. 30° C.). The outer casing 52 has a light transmitting portion 61 and a light transmitting portion 62 formed therein corresponding to opposite sides of the container 51, respectively. Passage apertures are formed in positions corresponding to the entering light transmitting portion 61 and exiting light transmitting portion 62 of the outer casing 52. Opal glass G is mounted to be maintained in a sealed condition to act as a diffuser.

Figure 10:
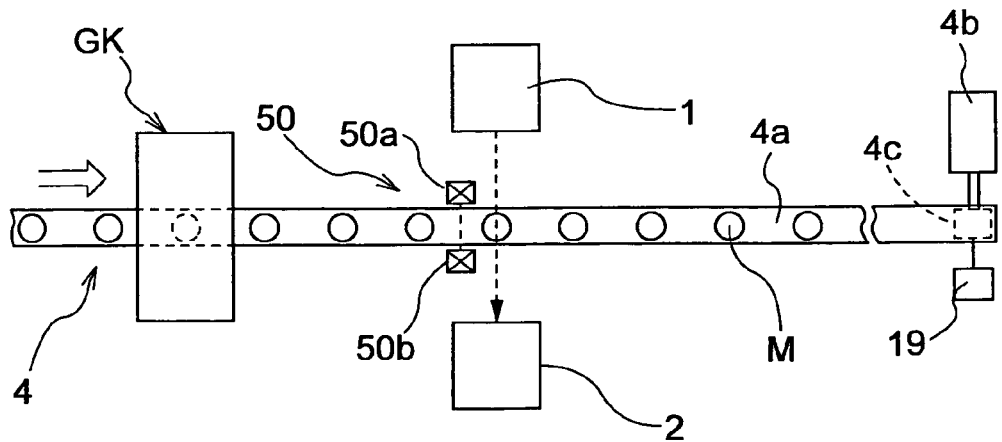
FIG. 10 is a plan view showing an installed state of the quality evaluation apparatus.

As shown in FIG. 10, the transport conveyor 4 includes an endless rotatable belt 4*a* driven by an electric motor 4*b*. The endless rotatable belt 4*a* is wound around a rotary member 4*c* having a rotational axis with a rotary encoder 19 acting as a transporting distance measuring device for detecting a transporting distance by the transport conveyor 4. The information detected by the rotary encoder 19 is inputted to the control section 3. Further, a passage detecting sensor 50 of the optical type is provided upstream of the position for measurement in the transporting direction to act as an object detecting device. This passage detecting sensor 50 detects whether a forward end of each measured object transported by the transport conveyor 4 has reached an upstream position in the transporting direction before the position for measurement. The passage detecting sensor 50 includes a light emitter 50*a* for emitting light and a light receiver 50*b* for receiving the light, the light emitter and light receiver being distributed to opposite sides of the transport path of the transport conveyor 4. The presence of the measured object is detected when the light emitted by the light emitter 50*a* is intercepted by the object and cannot be received by the light receiver 50*b*.

Figure 9:
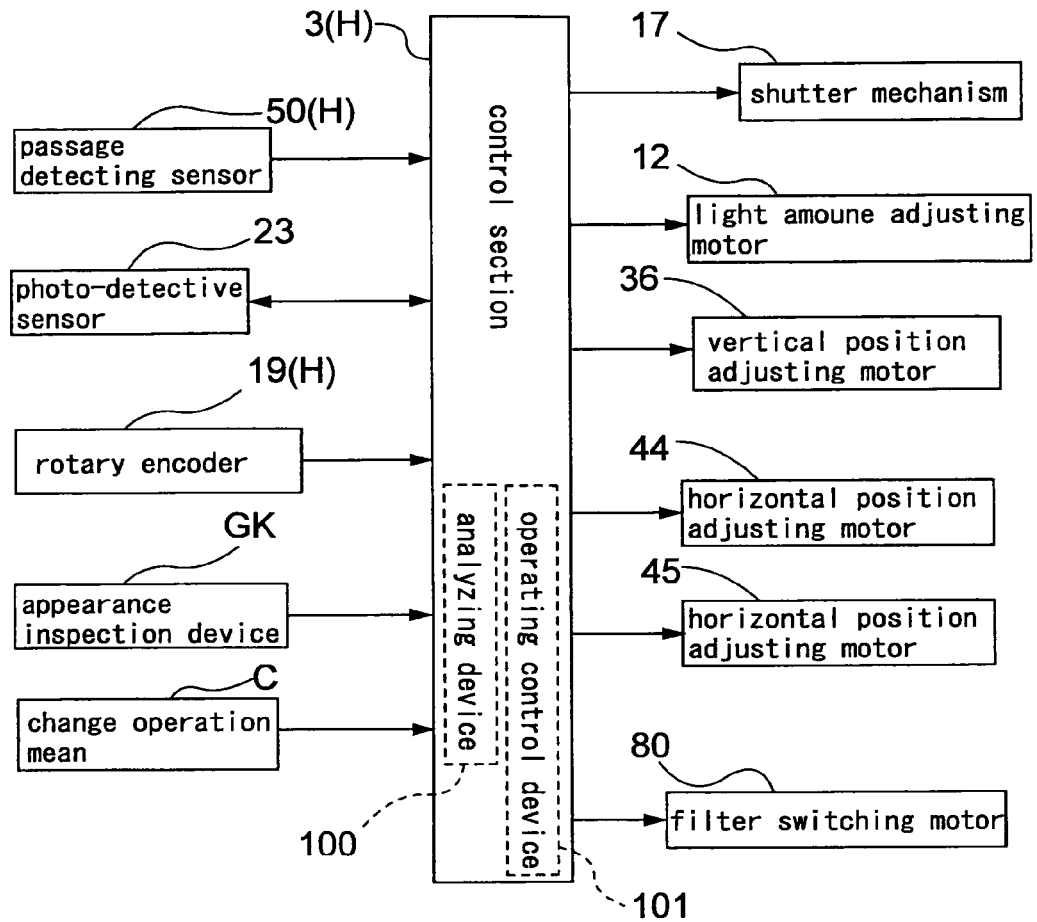
FIG. 9 is a control block diagram.

As shown in FIG. 9, the control section 3 utilizing a microcomputer includes, in the form of control programs, an analyzing device 100 acting as a computing section for analyzing the inner quality of the measured objects based on detection information from the passage detecting sensor 50, rotary encoder 19 and photo-detective sensor 23, and an operation control device 101 for controlling the operations of the respective sections. More particularly, the conventional spectral analyzing method described hereinafter is used for executing a computing process for analyzing the inner quality of measured objects M, while controlling the operations of the respective components such as the shutter mechanism 17, light amount adjusting motor 12, filter switching motor 80, vertical position adjusting motor 36 and horizontal position adjusting motors 44 and 45.

(Control Operation By the Control Section)

The control section 3 executes two data measurement processes. One is a reference data measurement process in which light is emitted from the light emitting section 1 to the reference filter 49 instead of the measured objects M, and transmitted light from the reference filter 49 is separated at the light receiving section 2 into rays, thereby to determine spectral data obtained by the separated rays as reference spectral data. The other is a normal data measurement process in which light is emitted from the light emitting section 1 to the measured objects M transported by the transport conveyor 4 to obtain measurement spectral data for analyzing the inner quality of the objects M based on the measurement spectral data and the reference spectral data.

(Reference Data Measurement Process)

The reference measurement mode is selected by operating the vertical position adjusting mechanism 29, and the shutter mechanism 17 is switched to the open state, while suspending the transport by the transport conveyor 4 of the measured objects M. Light is emitted from the light emitting section 1 to the reference filter 49 in this state. The transmitted light from the reference filter 49 is separated into rays at the light receiving section 2 thereby to measure the spectral data obtained by receiving the separated rays as the reference spectral data. Also, values detected by a photo-detective sensor 18 (dark current data) are measured in an aphotic condition in which the light to the light receiving section 2 is blocked. More particularly, the shutter mechanism 17 of the light receiving section 2 is switched to the closed state to obtain the values detected by the photo-detective sensor 18 in each unit pixel as dark current data.

(Normal Data Measurement Process)

In this normal data measurement process, the vertical position adjusting mechanism 29, specifically the vertical position adjusting electric motor 36, is operated to switch the lift deck 34 to the normal measurement mode, and the transport conveyor 4 is operated to transport the measured objects M. When no measured object is present in the position for measurement, or when photo-detective information for quality evaluation, as described hereinafter, has already been obtained even if a measured object is present in the position for measurement, a charge storage discharge process is repeatedly executed for allowing the photo-detective sensor 23 to be stored in until a predetermined charge storage time elapses from start of the charge storage and then releasing the charges stored in the photo-detective sensor 23 until a predetermined discharge time elapses. When a measured object transported by the transport conveyor 4 reaches the position for measurement, the charges stored in the photo-detective sensor 23 are released until the predetermined discharge time elapses after that time. Then, the measurement charge storage process is executed for storing charges for use as the photo-detective information for quality evaluation in the photo-detective sensor 23 until a predetermined measurement time elapses.

Figure 12:
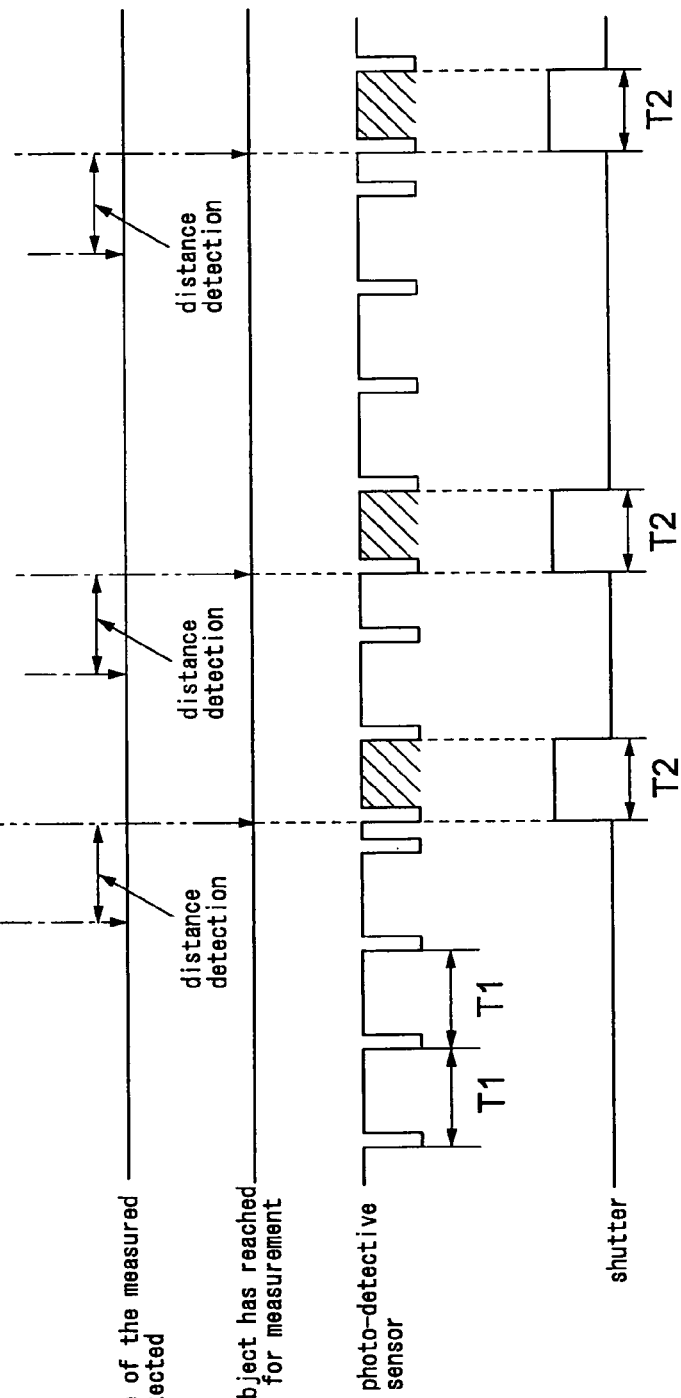
FIG. 12 is a timing chart of measurement operation.

More particularly, as shown in FIG. 12, the control section 3 constantly allows charges to be stored in the photo-detective sensor 23 until the predetermined charge storage time (approximately 40 msec) elapses from start of the charge storage when no measured object is present in the position for measurement or when photo-detective information for quality evaluation has already been obtained even if a measured object is present in the position for measurement. Subsequently, the control section controls the operation of the photo-detective sensor 23 in order to repeatedly execute the charge storage discharge process in predetermined cycles T1 (approximately 50 msec) for releasing the charges stored in the photo-detective sensor 23 until the predetermined discharge time (approximately 10 msec) elapses.

Then, the control section 3 detects the forward end of a measured object reaching the upstream position based on the information detected by the passage detecting sensor 50, and determines that the measured object has reached the position for measurement based on the information detected by the rotary encoder 19. Specifically, as the passage detecting sensor 50 detects that the forward end of the measured object M reaches the upstream position in the transporting direction which is a position for detection by the passage detecting sensor 50, it is determined whether or not the transporting distance of the measured object from that point of time agrees with the transporting distance from the upstream position to the position for measurement based on the information detected by the rotary encoder 19. When the transporting distance has been covered, it is determined that the measured object M has reached the position for measurement.

When it is determined that the measured object M has reached the position for measurement, instead of the charge storage discharge process repeatedly executed, the charges stored in the photo-detective sensor 23 are released until the predetermined discharge time elapses from that point of time as shown in FIG. 12. Subsequently, the measurement charge storage process is executed for storing charges for use as the photo-detective information for quality evaluation in the photo-detective sensor 23 until the predetermined measurement time elapses. The control section 3 also switches the shutter mechanism 17 from the closed state to the open state as the measured object reaches the position for measurement, in parallel to switching of the operation of the photo-detective sensor 23. The shutter mechanism 17 is maintained in the open state until the shutter opening time T2 elapses for executing the charge storage, and is then returned to the closed state. Thus, the light emitted from the light emitting section 1 and separated at the light receiving section 2 into rays may be stored as charges in the photo-detective sensor 23, until the predetermined measurement time lapses after the shutter mechanism 17 is opened. The shutter mechanism 17 is opened for a period of time combining the predetermined discharge time with the predetermined measurement time. In the example shown in FIG. 12, the predetermined discharge time is set to a period of time, approximately 10 msec, for example, required for the measured object to move to a position where stray light from the light emitting section 1 does not directly enter the light receiving section 2. This example shows that the predetermined measurement time is approximately 40 msec while the shutter opening time T2 is approximately 50 msec. After lapse of the shutter opening time T2, the stored charges are fetched to obtain measurement spectral data as the photo-detective information for quality evaluation.

The predetermined measurement time is varied according to the kind of measured objects or the like. In the case of apples or the like, for example, a longer period of time is selected (approximately 40 msec as noted above) since light is not easily transmitted therethrough. In contrast, in the case of mandarin oranges through which light is relatively easily transmitted, a relatively short period of time is selected (approximately 10 msec). The transporting speed of the transport conveyor 4 may be appropriately selected taking account of the size of measured objects or the measurement time noted above. More particularly, in the case of apples where the predetermined charge storage time (approximately 40 msec) is substantially the same as the predetermined charge storage time in the charge storage discharge process, and a maximum time for charge storage is selected. In the case of mandarin oranges, a shorter period of time is selected.

Figure 11:
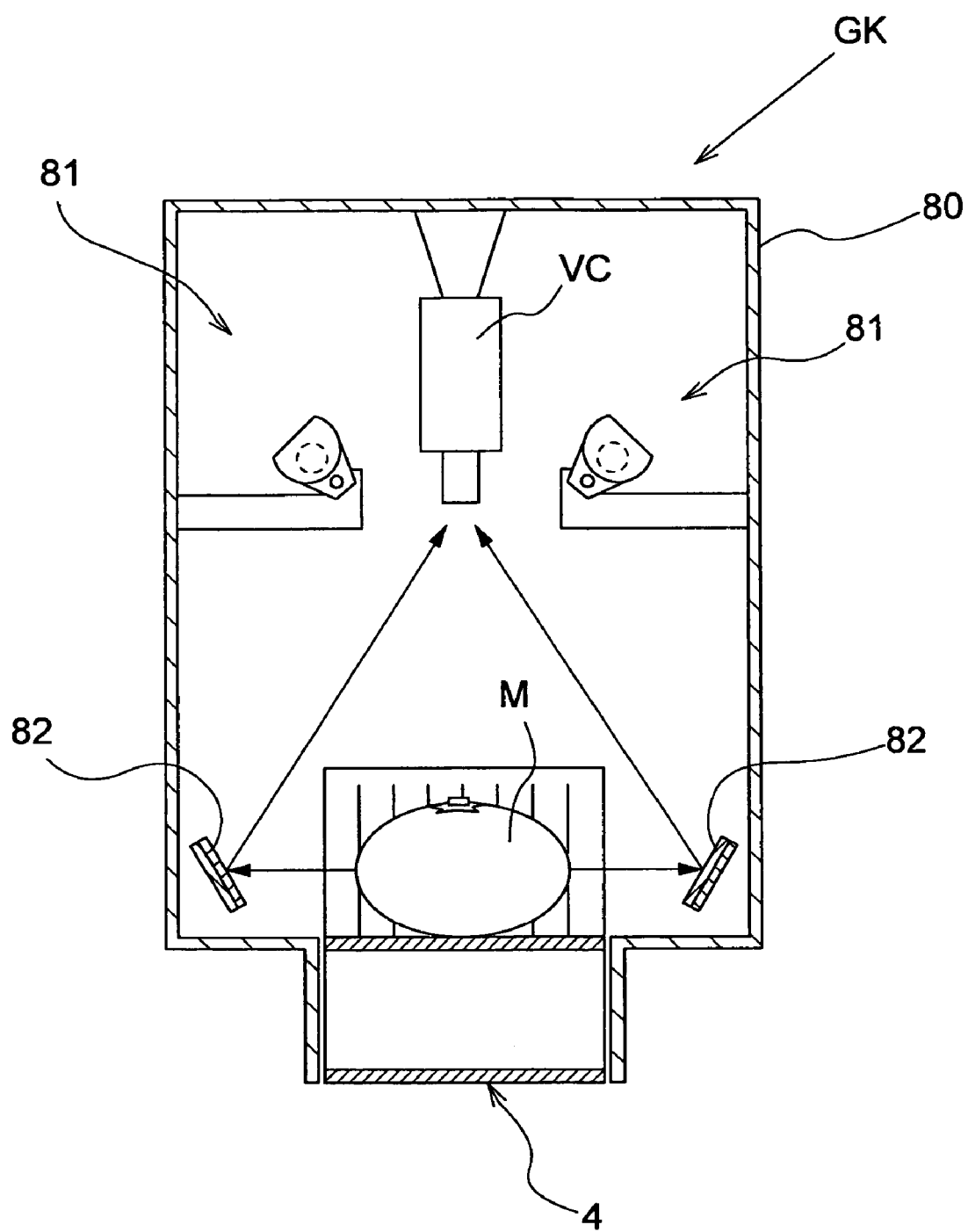
FIG. 11 is a view showing an appearance inspection device.

Operating conditions are determined with differences in the kind automatically instead of being switched manually. As shown in FIG. 10, this embodiment provides an appearance inspection device GK, apart from the quality evaluation apparatus, which is arranged upstream in the transporting direction of the transport conveyor 4 for inspecting the appearance of objects transported to be measured. The kind is determined utilizing a detection result from the appearance inspection device GK thereby to automatically select the operating conditions according to the difference in the kind. As shown in FIG. 11, the appearance inspection device GK includes a color video camera VC arranged inside a shielding cover 80 for imaging the measured objects. A known image processing method is used on the image information obtained from the video camera VC to determine outer dimensions and presence of abnormalities in appearance such as color irregularities. Such information is utilized, along with evaluation results obtained from the quality evaluation apparatus, for ranking fruits and vegetables. The appearance inspection apparatus GK includes also a lighting device 81 for indirectly illuminating the measured objects, and reflecting mirrors 82 for imaging side faces of the measured objects. The control section 3 receives measurement results from the appearance inspection device GK to determine the kind, and varies and adjusts the predetermined measurement time based on the determination.

A computing process is executed for analyzing the inner quality of the objects M by using a known spectral analysis technique based on the reference spectral data, the dark current data and the measurement spectral data obtained in this manner.

Specifically, a normalization is executed by using the reference spectral data and the dark current data obtained in the reference data measurement mode to obtain absorbance spectral data in each wavelength of the separated rays. Then, the second derivatives of the absorbance spectral data are obtained. More particularly, the absorbance spectral data is obtained corresponding to the photo-detective information obtained in each unit photo-detector of the photo-detective sensor 23. A quality evaluation process is executed for calculating a component amount corresponding to a sugar content and a component amount corresponding to an acid degree of the measured objects M as quality evaluation values based on the second derivatives in particular wavelengths for calculating the component amounts, of the obtained second derivatives of the absorbance spectral data, and on a predetermined calibration formula.

Thus, in this embodiment, a control unit H for controlling the operations of the respective components obtains the inner quality information of the measured objects, based on the photo-detective information from the light receiving section 2 by the control section 3, passage detecting sensor 50 and rotary encoder 19.

The absorbance spectral data d is obtained from the following formula where the reference spectral data is Rd, the measurement spectral data is Sd, and the dark current data is Da:

$$d = \log[(Rd-Da)/(Sd-Da)] \qquad \text{[Formula 1]}$$

Then, the obtained absorbance spectral data d is put to a quadratic differentiation. The second derivatives in the particular wavelength of the values thereby obtained and the calibration formula indicated below as Formula 2 are utilized to obtain calibration values for calculating the component amounts corresponding to the sugar content and acid degree contained in the measured objects M.

$$Y = K0 + K1 \cdot A(\lambda 1) + K2 \cdot A(\lambda 2) \qquad \text{[Formula 2]}$$

where;
Y: calibration value corresponding to the component amount
K0, K1, K2: coefficients
A (λ1), A (λ2): second derivatives in the particular wavelength λ of the absorbance spectral data.

A particular calibration formula, particular coefficients K0, K1 and K2, and particular wavelengths λ1, λ2 are predetermined and stored in advance for each component to be measured. The computing device 100 computes a measurement value (component amount) for each component utilizing the particular calibration formula.

(Wavelength Calibrating Process)

The wavelength calibrating process is executed by the analyzing device 100, and consists of a measuring process for calibration data executed prior to the normal measurement of the measured objects M and a converting process of the measurement data obtained by the normal measurement of the measured objects M.

The measuring process for calibration data will be described first. The rotary member 81 is rotated by the filter switching motor in the filter switching mechanism E prior to the normal measurement, thereby to position the wavelength calibrating filter 84 in the light passage. The light from the light emitting section 1 is emitted to the filter as it is to determine a wavelength received by each unit photo-detector 23a of the photo-detective sensor 23 based on the photo-detective information obtained by the light receiving section 2. Specifically, the wavelength calibrating filter is formed as a reference object for wavelength calibration having characteristics in light transmission in particular wavelengths of near-infrared light, and further specifically, having peaks in light transmission in at least a pair of known particular wavelengths.

Therefore, the light having transmitted through the wavelength calibrating filter has transmitted light amount peaks W1 and W2 in the pair of particular wavelengths (λ1, λ2) as shown in FIG. 14(a). The above-noted photo-detective sensor 23 detects the light and relates at least a pair of unit photo-detectors 23a having the maximum light receiving amounts to the known wavelengths (λ1, λ2) of the light having the transmitted light amount peaks W1 and W2, thereby to realize the wavelength calibrating process. When the pair of unit photo-detectors 23a of the photo-detective sensor 23 receiving the pair of predetermined wavelengths (λ1, λ2) have a pair of element numbers (P1, P2), the light receiving wavelengths λ in the other unit detectors 23a (element numbers P) are represented by the following formula 3 which is a linear approximation formula where the element number P is a variable for obtaining a wavelength corresponding to each element number. In the formula, "a" is a gradient of the linear approximation formula and "b" is an intercept obtained virtually for the purpose of calculation. This formula may be graphically shown as in FIG. 14(b).

$$\lambda = aP + b \qquad \text{[Formula 3]}$$

Next, the converting process of the measurement data will be described. The second derivative of the absorbance spectral data in each wavelength obtained by the above-noted normal data measurement process is data having reference to the light receiving position corresponding to the photo-detective information obtained in each of the 1024 unit photo-detectors 23a of the photo-detective sensor 23. In the converting process of the measurement data, the second derivative of the absorbance spectral data of the wavelength corresponding to the particular wavelength for calculating the components of the measured objects is obtained by interpolation through an arithmetic processing based on Formula 3. Then, the data obtained with reference to the light receiving position for each unit photo-detector 23a as noted above is converted to the data with reference to a correct wavelength.

The light incident on the spectroscope 18 is limited by the band-pass mirror 15 to a particular wavelength range of 680 nm through 990 nm to be measured. Further, in the wavelength calibrating process, the wavelength in each unit photo-detector 23a is determined based on all the photo-detective data in the 1024 unit photo-detectors 23a of the photo-detective sensor 23. Thus, a wavelength resolution becomes around 0.3 nm in determining the wavelengths of the separated rays for executing the wavelength calibrating process.

Figure 15:
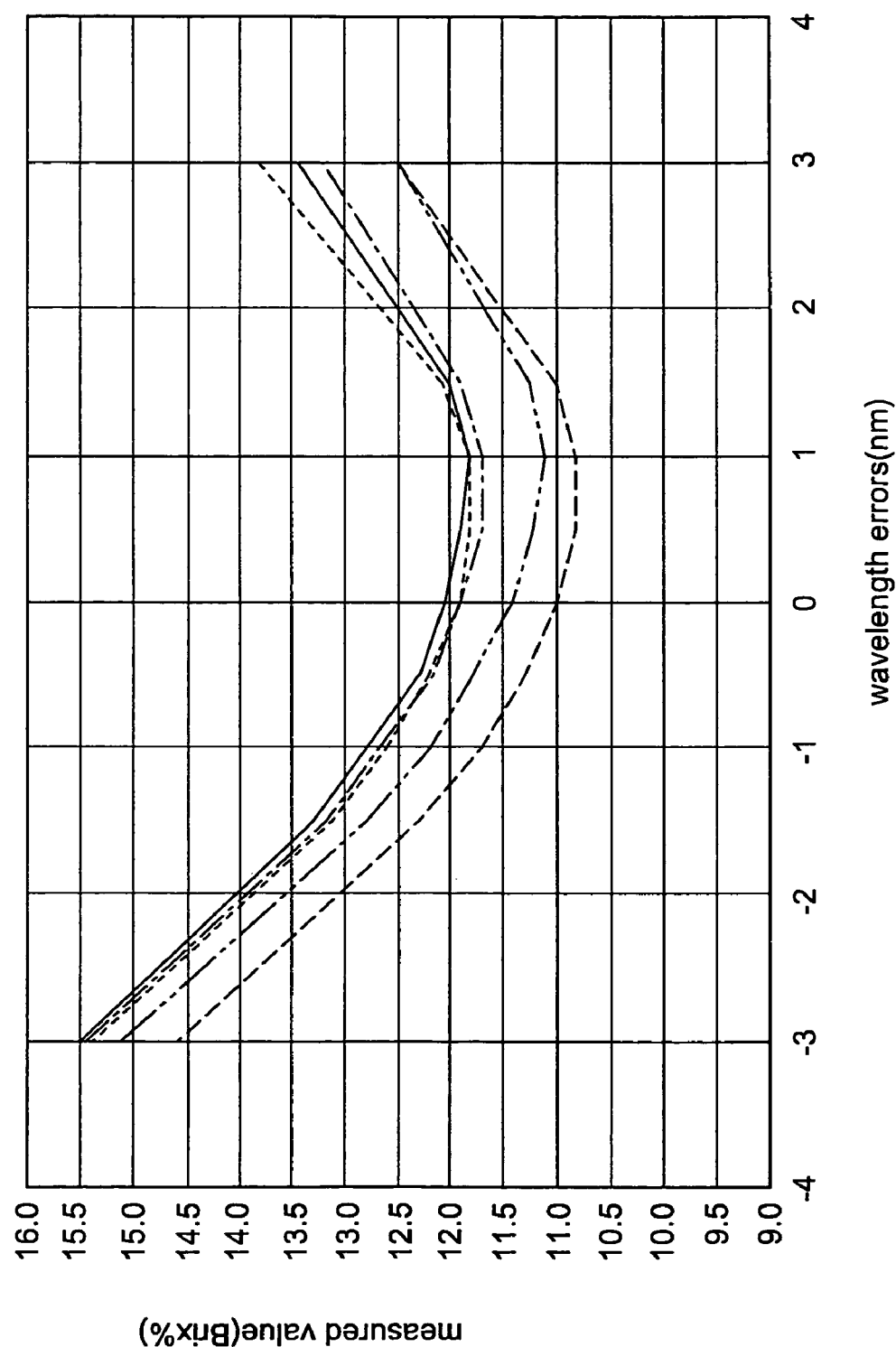
FIG. 15 is a graph showing a relationship between sugar measurement value and wavelength error.

In the case of fruits and vegetables such as oranges or apples, measurement errors required as measurement accuracy of the sugar content as the quality evaluation value should generally be 0.5 degrees or less. However, as apparent from FIG. 15 showing experimental data presented by the applicant, the required measurement accuracy of 0.5 degrees or less will be achieved when the wavelength resolution which is a factor of wavelength errors is 0.3 nm.

(Procedure for Establishing Calibration Formula)

A calibration formula is individually determined for each apparatus based on the data obtained by actually measuring samples similar to the measured objects in advance. More particularly, when various kinds of fruits and vegetables are to be measured as described above, a calibration formula is established and stored individually for each kind.

First, the process for establishing a calibration formula for one kind of measured object will be described.

A measurement process for calibration data of the wavelength calibrating process is executed as noted above to establish the relationship represented by Formula 1 in order to determine the wavelength of the light received by each unit photo-detector 23a of the photo-detective sensor 23.

Next, tens or hundreds of measured objects are prepared as samples. The spectral data is obtained for each wavelength by utilizing the spectral analysis device in each sample. Further, absorbance spectral data is obtained from the spectral data as noted above. The absorbance spectral data obtained in this manner is data obtained for each of the 1024 unit photo-detectors 23a of the photo-detective sensor 23.

Then, the converting process of the measurement data is executed for obtaining absorbance data for establishing the calibration formula with respect to the obtained absorbance spectral data. In this case, the absorbance spectral data is obtained corresponding to wavelengths varying every 2 nm from 700 nm as correct wavelengths. In other words, the absorbance spectral data is obtained from each unit photo-detector 23a corresponding to the corresponding wavelength based on the absorbance spectral data obtained from each of the 1024 unit photo-detectors 23a of the photo-detective sensor 23 and the relational expression represented by Formula 1. More particularly, the absorbance spectral data is obtained in each of the correct wavelengths of 700, 702, 704 and so on. In the case of obtaining the absorbance spectral data every 2 nm from 700 nm to 990 nm, the number of data is around 145.

Further, a detection process for actual component amounts is executed for accurately detecting chemical components of the measured objects by a special inspection device based on a destructive analysis or the like, for example, thereby to obtain actual component amounts of the measured objects. Then, the absorbance spectral data obtained from each sample as noted above is used and compared with the detected results of the actual component amounts, and the calibration formula is established for representing the relationship between the absorbance spectral data and the amount of a particular component by using the multiple regression analysis technique.

At this time, the calibration formula is established by calculation based on about 145 data as described above, instead of using all the 1024 unit photo-detectors 23a of the photo-detective sensor 23, which can save time and effort in establishing the calibration formula.

Thus, according to this quality evaluation apparatus, the calibration formula is established by using the photo-detective information with the resolution (2 nm) greater than the maximum resolution (0.3 nm) of the photo-detective information determined with the number (1024) of the plural unit photo-detectors 23a of the photo-detective sensor 23. The analyzing device 100 acing as computing section is arranged to execute the wavelength calibrating process with the resolution less than the resolution (2 nm) for establishing the calibration formula and yet with the maximum resolution (0.3 nm) of the photo-detective information determined with the number (1024) of the plural unit photo-detectors 23a of the photo-detective sensor 23.

The calibration formulas are determined and stored for a plurality of kinds through the above method. Which calibration formula is utilized by the control section 3 in the measurement process is automatically determined in the same way as in varying and adjusting the predetermined measurement time T4 based on the measurement results obtained from the appearance inspection device as noted above.

(Other Embodiment Relating to the Light Emitting Section and Light Receiving Section)

Next, a second embodiment of the present invention will be described.

The quality evaluation apparatus in this embodiment is different from the quality evaluation apparatus in the first embodiment only in the arrangement of the light emitting section 1 and light receiving section 2, the light passage arrangement with respect to the light receiving section 2, the construction of the transport conveyor and the measurement method by the photo-detective sensor 23. Only the different constructions will be described hereinafter. The light emitting section 1 and light receiving section 2 are formed as units, respectively, and have substantially the same constructions as in the first embodiment.

Figure 16:
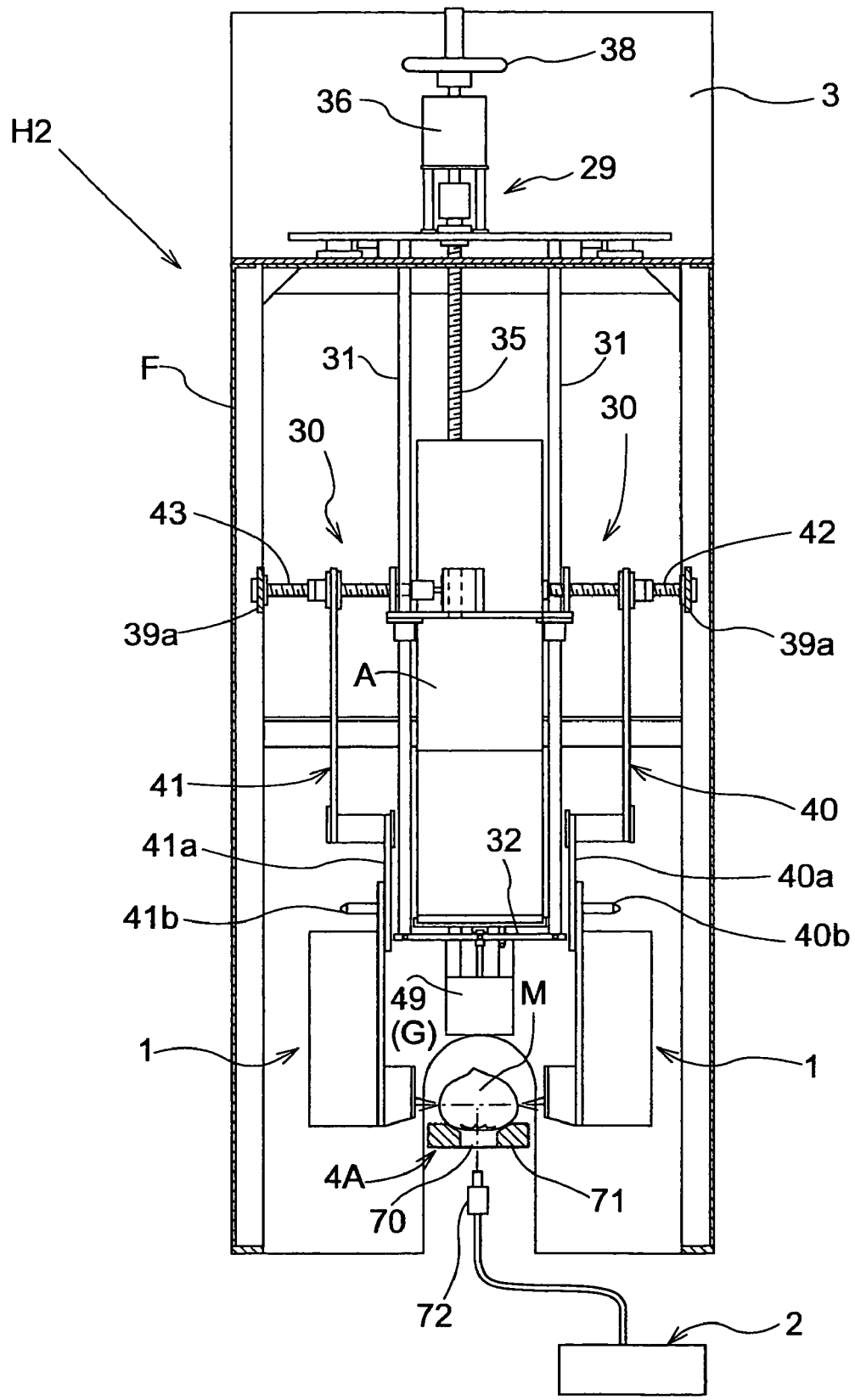
FIG. 16 is a front view of a quality evaluation apparatus according to a modified embodiment.

As shown in FIG. 16, two light emitting sections 1 of the unit type having the same construction as the light emitting section 1 of the first embodiment are provided. Those two light emitting sections 1 are distributed to opposite sides of the position for measurement, namely opposite sides of a transport conveyor 4a in the direction of width thereof. The light emitting direction of each light emitting section 1 is substantially horizontal. However, the mounting seats 40a and 41a provided at the lower ends of the support members 40 and 41 are the same and correspond to the vertical length of the light emitting section 1. The inclining position limiting element 40c used in the foregoing quality evaluation apparatus is not used so that the light emitting direction of each light emitting section 1 may be substantially horizontal.

The transport conveyor 4A transports the measured objects as placed in saucers 71 having an aperture 70 formed in the central portion thereof. Disposed below the saucers 71 is a light receiving end 72 of an optical fiber for receiving the light emitted from the light emitting sections 1 and transmitted through the measured objects and further transmitted downward through the apertures 70 of the saucers 71. To the other end of the optical fiber 72 is connected the light receiving section 2 of the unit type having substantially the same construction as in the first embodiment. The analyzing process of inner quality is executed in the control section 3 based on the photo-detective information provided by the light receiving section 2 in the same way as in the first embodiment.

In this quality evaluation apparatus, light is emitted from the right and left light emitting sections 1 in a substantially opposed relationship in the horizontal direction to a measured object lying in the position for measurement. The light is scattered within the measured object transmitted downward to be received by the optical fiber 72 and guided to the light receiving section 2.

Thus, in this arrangement with the light emitting sections 1 and the light receiving section 2 mounted in place, respectively, the light emitting sections 1 and the light receiving section 2 are arranged so that the light emitting positions where the light emitting sections 1 are disposed, the position for measurement and the light receiving position where the light receiving section 2 is disposed are arranged on bent lines.

The transport conveyor 4A transports the measured objects M placed in particular positions on the saucers 71. More particularly, the saucers 71 are made of a soft material such as rubber or the like, and have an outer configuration of a cylindrical shape in plan view with the circular aperture 70 formed in the central portion thereof as shown in FIG. 17. The aperture 70 has an inclined upper portion at an outer periphery thereof directed downward toward the center. When fruits or vegetables such as peaches, pears, apples or the like having a generally spherical shape, which are an example of measured objects M, are placed on the saucers 71, the objects rest substantially coaxially with the apertures 70 by gravity. In other words, the center position of each saucer 71 corresponds to the particular position noted above.

The saucers 71 are the free carrier type placed on an endless rotatable belt 4d of the transport conveyor 4A, and are transported by pushing action of pushing elements 4e arranged on the endless rotatable belt 4d at predetermined intervals in the transporting direction. The opposite sides of the saucers in the width direction are guided by limiting elements 4f arranged in the transporting direction. The saucers 71 have lower portions at the middle in the width direction of the endless rotatable belt 4d, which are opened for allowing the light emitted from the light emitting sections 1 and transmitted through the measured objects M to be received at the light receiving end of the optical fiber 72.

In this embodiment, as shown in FIG. 18, an optical, saucer detecting sensor 73 is provided for detecting forward ends of the saucers 71 in the transporting direction reaching a predetermined position. The saucer detecting sensor 73 includes a light emitter 73a for emitting light and a light receiver 73b for receiving the light, the light emitter and light receiver being distributed to opposite sides of the transporting passage of the transport conveyor 4A. That the forward ends of the saucers 71 in the transporting direction have reached the predetermined position is detected when the light emitted by the light emitter 73a is blocked by the saucers 71 which are the detected objects and cannot be received by the light receiver 73b.

Then, the control section 31 determines that the measured objects M have reached the position for measurement based on detection information from the saucer detecting sensor 73. More particularly, when the saucer detecting sensor 73 detects that the forward ends of the saucers 71 in the transporting direction have reached the predetermined position, the control section determines that the measured objects M have reached the position for measurement and immediately executes the same measurement charge storage process as the measurement charge storage process in the first embodiment noted above.

More particularly, a positional relationship between the saucer detecting sensor 73 and the light receiving end of the optical fiber 72 is determined beforehand so that, when the saucer detecting sensor 73 detects that the forward ends of the saucers in the transporting direction have reached the predetermined position, the light receiving end of the optical fiber 72 lies in an upstream position of the apertures 70 in the transporting direction in plan view. It is to be noted that the respective light emitting sections 1 are substantially aligned in the direction of width of the transporting direction with the light receiving end of the optical fiber 72.

When the saucer detecting sensor 73 detects that the forward ends of the saucers in the transporting direction have reached the predetermined position, the measurement charge storage process is immediately executed. This allows the light transmitted from the measured objects to be received properly at the light receiving end of the optical fiber 72.

Figure 19:
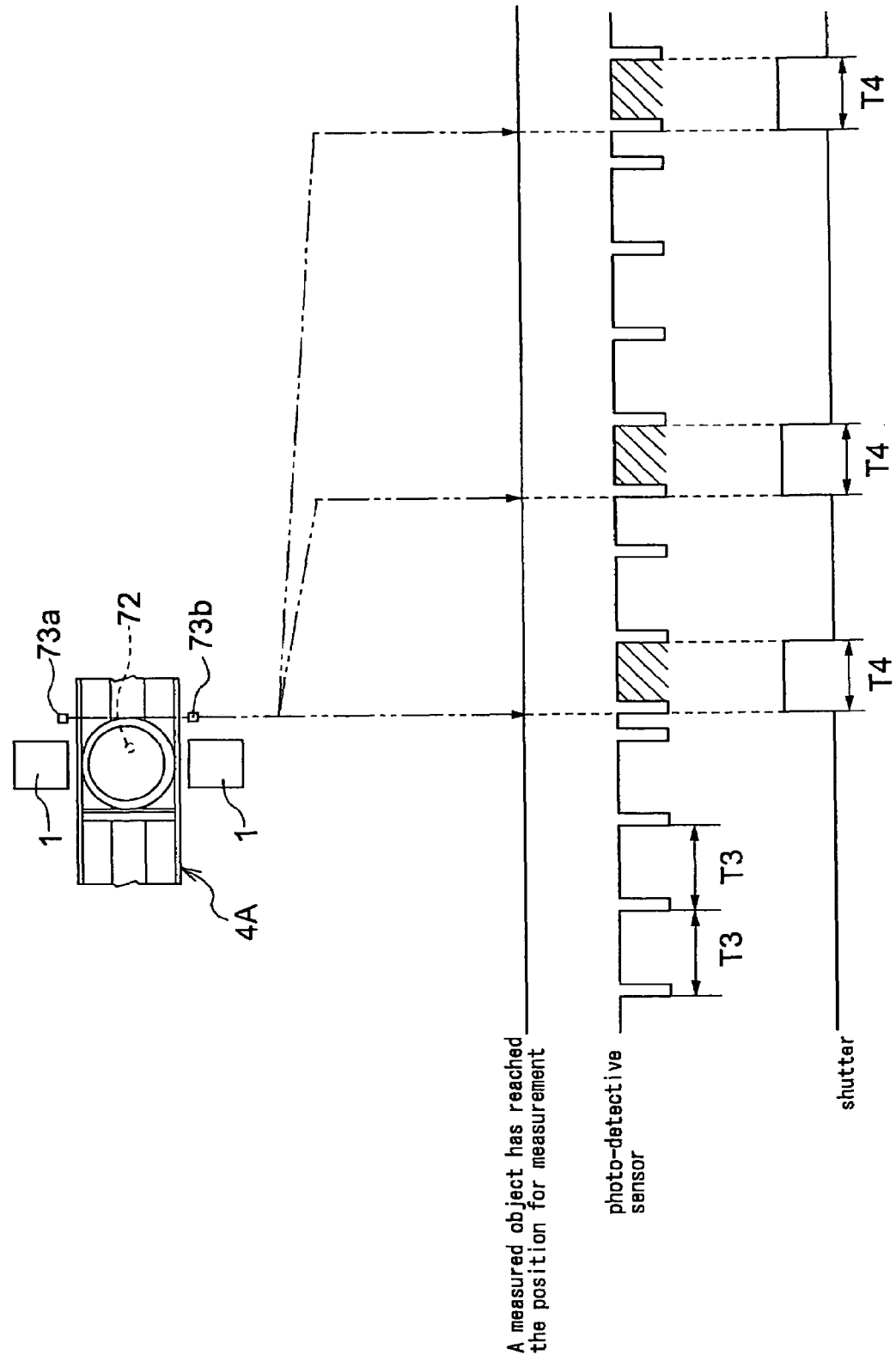
FIG. 19 is a timing chart of measurement operation according to the modified embodiment.

As shown in the timing chart of FIG. 19, the control section 3 executes the measurement charge storage process immediately after the saucer detecting sensor 73 detects that the forward ends of the saucers 71 in the transporting direction have reached the predetermined position. In parallel, the control section switches the shutter mechanism 17 from the closed state to the open state and controls the operation of the shutter mechanism 17 to maintain the open state until the shutter opening time T4 elapses and then reinstate the shutter mechanism in the closed state.

In this arrangement, the measurement charge storage process is executed immediately after the saucer detecting sensor 73 detects that the forward ends of the saucers 71 in the transporting direction have reached the predetermined position. Thus, it is possible to detect accurately that the measured objects have reached the position for measurement with reduced measurement errors caused by slippage or shaking of the transport conveyor and free from the influence of variations in the transporting speed or the like of the transport conveyor 4A.

In this embodiment, the control section 3 and the saucer detecting sensor 73 cooperate to obtain the inner quality information of the measured objects based on the photo-detective information of the light receiving section 2, and constitute the control unit H for controlling the operations of the respective components.

In this embodiment, as in the first embodiment, as shown in FIG. 19, the control section 3 controls the operation of the photo-detective sensor 23 in order to constantly execute the charge storage discharge process in predetermined cycles T3 repeatedly for allowing the charges to be stored in the photo-detective sensor 23 until the predetermined charge storage time elapses from the start of charge storage and then releasing the charges stored in the photo-detective sensor 23 until the predetermined discharge time elapses when no object to be measured is present in the position for measurement or when the photo-detective information for quality evaluation has already been obtained even if an object to be measured is present in the position for measurement.

(Other Embodiment Relating to the Position for Measurement)

A shading member 90 is provided in the position for measurement to act as a shading device for allowing the measured objects M to pass therethrough while blocking stray light of the light emitted from the light emitting section 1, which is about to enter the light receiving section 2 without being transmitted through the objects M.

Figure 20:
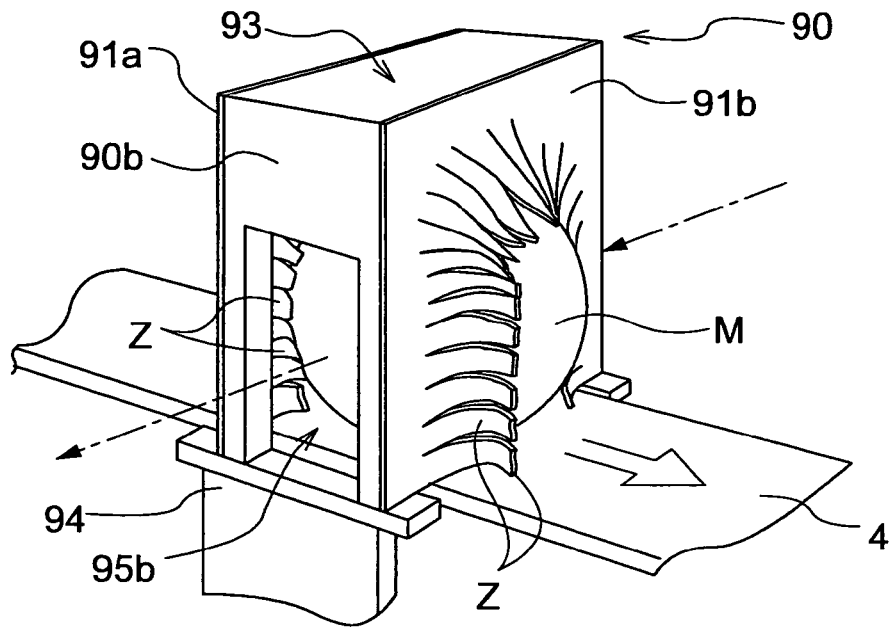
FIG. 20 is a perspective view of a shading device according to a further modified embodiment.
Figure 21:
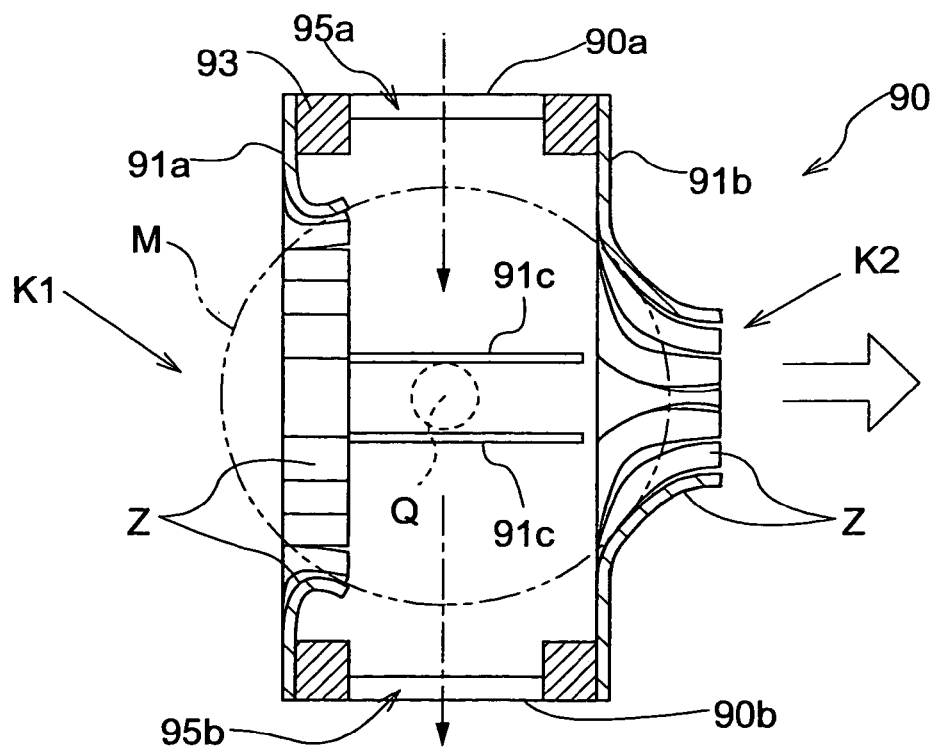
FIG. 21 is a plan view of the shading device according to the further modified embodiment.
Figure 22:
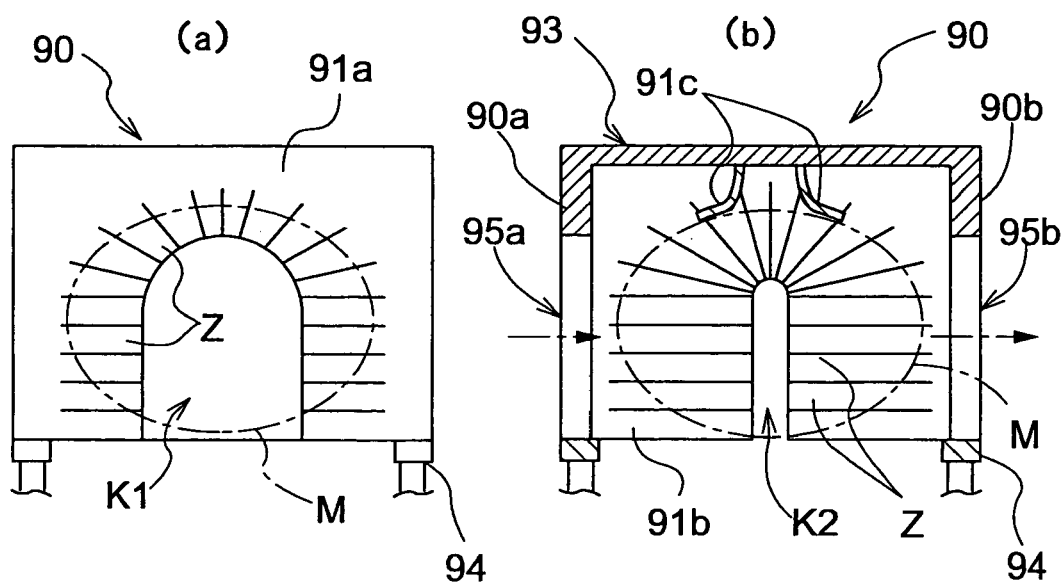
FIG. 22 is a front view of the shading device according to the further modified embodiment.

As shown in FIGS. 20 through 22, the shading member 90 comprises a frame element 93 made of a hard material formed in a substantially arched shape as viewed from the transporting direction of the measured objects M to allow the objects M to pass through a lower portion thereof. In side wall portions 90a and 90b positioned at opposite sides of the transporting direction are formed a light passage opening 95a for allowing passage of the light emitted to the measured objects M from the light emitting section 1, and a light passage opening 95b for allowing passage of the light transmitted through the measured objects M toward the light receiving section, respectively.

Shading elements 91a, 91b and 91c are provided on the frame element 93 in a side face upstream in the transporting direction, a side face downstream in the transporting direction and an upper position for blocking stray light in the upstream position of the transporting direction, the downstream position of the transporting direction, and the upper position from a light projecting position Q, for the measured objects M inside the frame element 93, i.e. the measured objects M placed in the position for measurement.

These shading elements 91a, 91b and 91c are made of a soft material having shading properties such as a thick cloth or a sponge material having shading properties, for example. Even though the measured objects M passing through the position for measurement may vary in size, the shading elements are retractable by bending and deforming along the surfaces of the measured objects M to allow passage of the objects without preventing the transport of the objects M. Further, the shading elements 91a and 91b provided upstream in the transporting direction and downstream in the transporting direction have openings K1 and K2 for allowing the measured objects M to be smoothly transported therethrough. The respective openings K1 and K2 have opening edge portions forming a plurality of flaps Z cut to have small gaps therebetween. Each flap Z is retractable by bending and deforming along the surfaces of the measured objects M to allow passage of the objects. Thus, it is possible to prevent stray light from entering the light receiving section 2 as much as possible by allowing the flaps to move smoothly along arcuate outer surfaces of the measured objects M even in the case of oranges or the like having a generally spherical shape.

(Other Embodiment Relating to the Normal Data Measurement Process)

The above-described normal data measurement process may be executed also by the following method.

Figure 23:
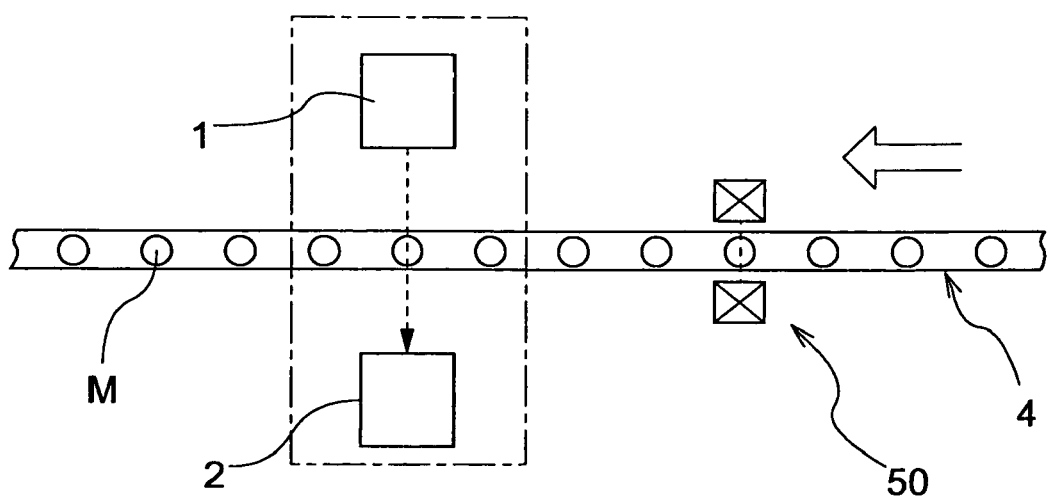
FIG. 23 is a front view of an installed state of the quality evaluation apparatus according to a still further modified embodiment.
Figure 24:
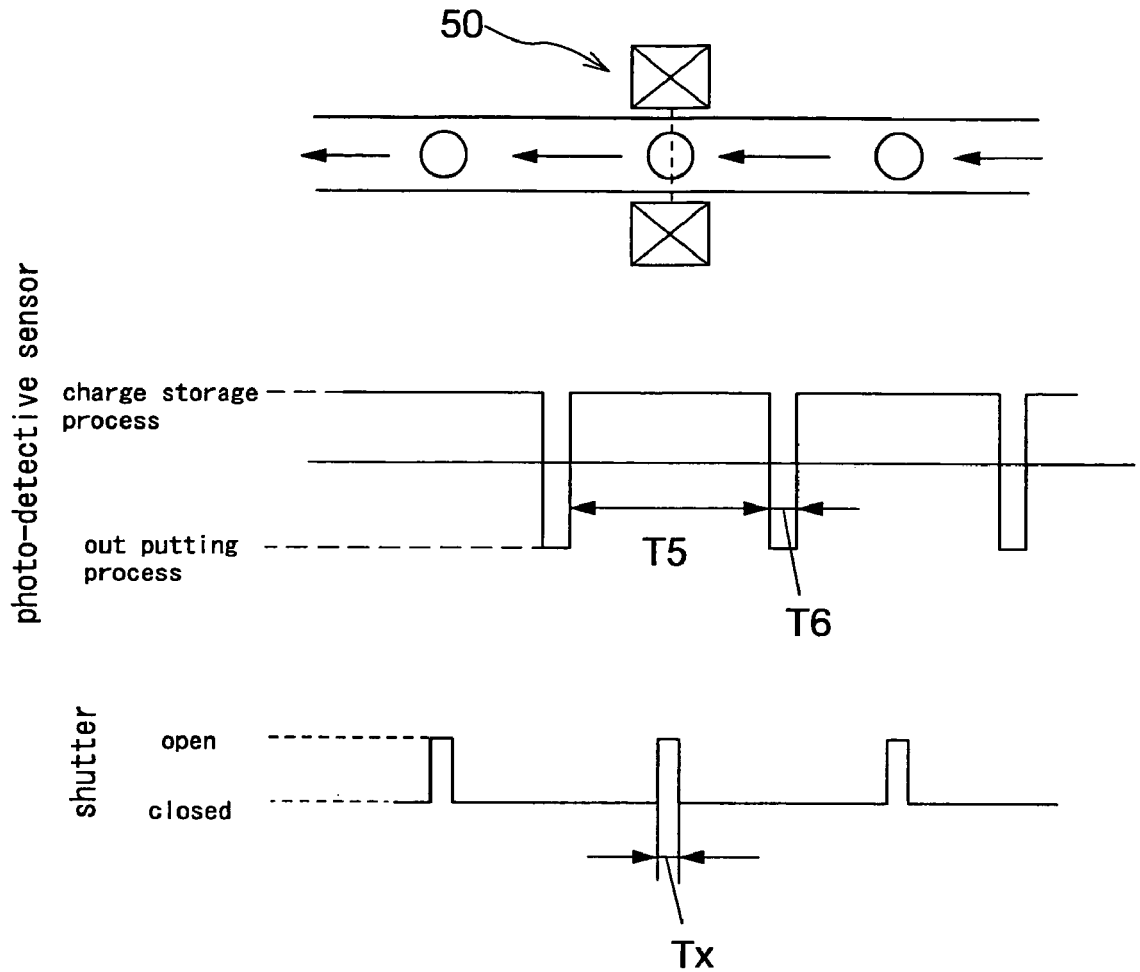
FIG. 24 is a timing chart of measurement operation according to the still further modified embodiment.

As shown in FIGS. 23 and 24, cycles in which the measured objects pass through the position for measurement are detected based on the detection information from the passage detecting sensor 50. The operation of the photo-detective sensor 23 is controlled to repeat, in predetermined cycles synchronized with the above cycles, the charge storage process for receiving the separated rays and executing the charge storage operation for a predetermined period of time and the outputting process for outputting the stored charges.

More particularly, the operation of the photo-detective sensor 23 is controlled such that the photo-detective sensor 23 executes the charge storage process only for a predetermined time T5 in a period of time in which each measured object M is expected to pass through the position for measurement, and executes the output process for outputting the stored charges for a predetermined time T6 when an intermediate position between the adjacent measured objects M coincides with the position for measurement and no object is expected to be present in the position for measurement. Thus, in this quality evaluation apparatus, the period of time for charge storage by the photo-detective sensor 23 is constant. In the case of a processing performance for passing seven measured objects per second, the predetermined time for executing the charge storage process will be around 140 msec.

The operation control device 101 controls the operation of the shutter mechanism 17 to switch the shutter mechanism, when the photo-detective sensor 23 is set to the position for measurement and the photo-detective sensor 23 executes the charge storage process, from the closed state to the open state to maintain the mechanism in the open state for an open state maintaining time Tx, and then reinstate the shutter mechanism in the closed state. The open state maintaining time Tx is varied and adjusted based on change command information.

The open state maintaining time Tx is varied with the kind of measured objects. More particularly, the time is set to a relatively short time (approximately 10 msec) in the case of mandarin oranges through which light is relatively easily transmitted, and to a longer time (approximately 30 msec) in the case of Iyo oranges through which light is not easily transmitted.

The operating conditions according to a difference in the kind are manually determined by the operator. As shown in FIG. 9, a switching element C is provided for the operator to manually switch a predetermined position according to a difference in the kind of objects. Setting information from the switching element C is inputted to the control section 3. The control section 3 varies and adjusts the open state maintaining time Tx in accordance with the setting information.

A process is executed for varying and adjusting the amount of light entering the spectroscope 18 by operating the filter switching mechanism noted hereinbefore according to the operating conditions determined as above.

Further, the operation control device 101 detects whether or not the measured objects have reached the position for measurement based on the received light amount detected by the light amount detecting sensor 19, i.e. variations in the actual measurement value of the amount of light transmitted through the measured objects. When it is detected that the measured objects have reached the position for measurement, the shutter mechanism 17 is switched to the open state which is maintained for the open state maintaining time Tx. Subsequently, the shutter mechanism 17 is switched to the closed state to complete the measurement process.

Figure 25:
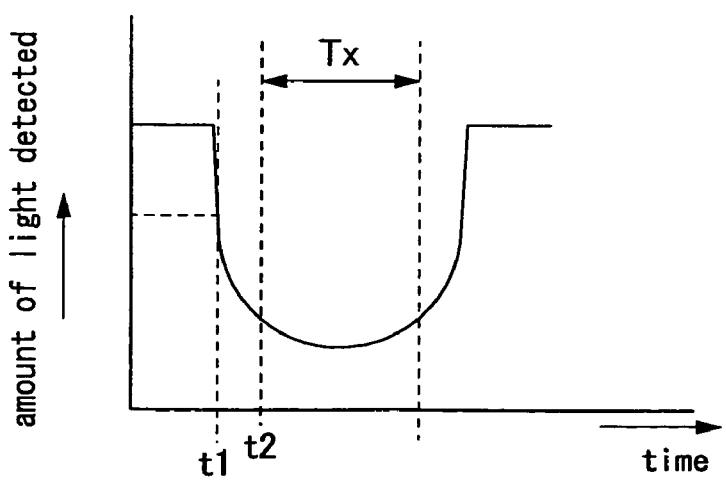
FIG. 25 is a chart showing variations of light amount and measurement timing according to the still further modified embodiment.

More particularly, FIG. 25 shows variations in the detection value of the light amount detecting sensor 19 occurring with passage of time. A substantially maximum value is outputted due to the light emitted from the light emitting section 1 until a measured object reaches the position for measurement. As the measured object M reaches the position for measurement, the measurement light is blocked and the detection value (received light amount) by the light amount sensor starts to decrease. When the detection value is reduced below a predetermined value (at t1), the measured object is determined to have reached the position for measurement and the shutter mechanism 17 is switched to the open state upon lapse of predetermined time (at t2) from that point of time. Then, the shutter mechanism 17 is switched to the closed state after being maintained in the open state for the open state maintaining time Tx.

When the transport conveyor 4 is stopped under abnormal conditions while such measurement process is being executed, the light amount adjusting plates 8 in the light emitting section 1 are switched to the blocking state to prevent a measured object standing still from being irradiated with strong light from the light sources for a long time.

(Further Embodiment Relating to the Normal Data Measurement Process)

FIG. 26 shows a timing chart of operation in this embodiment. As seen from this chart, when a detecting sensor similar to the passage detecting sensor 50 in the first embodiment detects that a saucer 71 or a measured object is transported to a position a predetermined distance short of the position for measurement, the measurement charge storage process is started by the photo-detective sensor 23 after a predetermined delay time T7 elapses from that point of time. The shutter mechanism 17 is switched from the closed state to the open state slightly before the charge storage process is executed and then switched from the open state to the closed state after a predetermined time T8 elapses.

In this embodiment, the photo-detective sensor 23 does not read the stored charge every time a measured object passes, but executes repeatedly a stored charge reading process whenever a predetermined time T9 (tens of msec, for example) elapses thereby to reduce residual charges. When the passage of a measured object is detected, the repeated process is reset at that point of time and the stored charge reading process is executed.

Other Embodiments (1) To determine whether or not a measured object has reached the position for measurement, the passage detecting sensor may directly detect whether a measured object has reached the position for measurement. More particularly, the position for detecting the upstream position of the measured object in the transporting direction by the passage detecting sensor may be set slightly upstream in the transporting direction of the light receiving position of the photo-detective sensor. When the upstream position of the measured object in the transporting direction is detected by the passage detecting sensor, the measurement charge storage process is immediately executed.

(2) As the detecting device for the measured objects, various components may determine that a measured object has reached the position for measurement every time the transport conveyor is moved a predetermined distance, based only on the information detected by the rotary encoder acting as the transporting distance measuring device, for example.

(3) In determining kinds of measured objects, it is possible to determine the kinds based on the measurement results of the measurement spectral data measured at the light receiving section, thereby to automatically determine operating conditions according to differences in kind. For example, the measurement spectral data is measured in advance with respect to a plurality of fruits and vegetables to be measured to check the characteristics thereof, and kinds are determined based on the characteristics when the objects are measured.

(4) In the second embodiment described hereinbefore, the saucer detecting sensor is provided to act as a saucer detecting device. When the saucer detecting sensor detects that the forward end in the transporting direction of a saucer has reached the predetermined position, the measurement charge storage process is immediately executed. Instead, as in the first embodiment, the saucer detecting sensor may detect first that the forward end in the transporting direction of a saucer has reached the position short of the predetermined position. Then, it may be determined that a measured object has reached the position for measurement based on the information detected by the rotary encoder.

(5) In the second embodiment described hereinbefore, the saucers are the free carrier type placed on the endless rotatable belt. Instead, the saucers may be connected to the endless rotatable belt as arranged at predetermined intervals.

(6) In the first embodiment described hereinbefore, the light emitting section and light receiving section are distributed to the opposite sides of the position for measurement. Instead, the light emitting section and light receiving section may be distributed to vertically opposite sides of the position for measurement.

(1) In the foregoing embodiments, the light receiving section acting as a photo-detector includes 1024 unit photo-detectors 23a for receiving rays in the particular wavelength range of 680 nm through 990 nm. The wavelength resolution in determining the wavelengths of separated rays is around 0.3 nm in order that the analyzing device acting as the computing section executes the wavelength calibrating process, while the resolution is around 2 nm in establishing the calibration formula. Instead, the following construction may be employed.

As the plural unit photo-detectors 23a, unit photo-detectors 23a may be smaller in number or larger in number than 1024.

The wavelength resolution in determining the wavelengths of separated rays may be properly varied below 0.8 nm in order for the analyzing device acting as the computing section to execute the wavelength calibrating process. The wavelength range may be properly varied as long as the range includes the wavelengths for evaluating the quality of the measured objects.

As the resolution in establishing the calibration formula, instead of establishing the calibration formula based on the photo-detective information obtained every 2 nm, the calibration formula may be established utilizing the photo-detective information obtained at larger intervals than 2 nm, namely with a greater resolution than in the foregoing embodiments.

(7) In the second embodiment described hereinbefore, the pair of light emitting sections are distributed to the opposite sides of the position for measurement, and the light transmitted downwardly of the position for measurement is received by the optical fiber to be guided to the light receiving section. Instead, a single light emitting section may be arranged at one side of the position for measurement. Instead of the construction for allowing the light to be received by the optical fiber, the light receiving section may be provided below the position for measurement to directly receive the transmitted light. The light emitting section and light receiving section may be juxtaposed at one side of the position for measurement, for example, thereby to receive the light emerging in the direction substantially opposite to the light emitting direction.

(9) In the foregoing embodiments, halogen lamps are utilized as the light sources of the light emitting section. Instead, various light sources including mercury lamps, Ne discharge tubes or the like may be used. The photo-detective sensor is not limited to the CCD type line sensor, but other detecting device such as a line sensor of the MOS type or the like may be used.

(2) In the foregoing embodiments, the analyzing device acting as the computing section executes the wavelength calibrating process with a maximum resolution of the photo-detective information determined by the number of plural unit photo-detectors 23a. Instead of such a construction, the resolution may be smaller than the resolution in establishing the calibration formula, and the wavelength calibrating process may be executed with a resolution greater than the maximum resolution.

(3) In the foregoing embodiments, the reference object for wavelength calibration has two or more particular wavelengths serving as the particular wavelength having the characteristics in light transmission. Instead of such a construction, the reference object may have one particular wavelength serving as the particular wavelength having the characteristics in light transmission. As the wavelength calibrating process, one unit photo-detector 23a may be determined to receive one particular wavelength, thereby to obtain the wavelengths received by the other unit photo-detectors 23a based on the positional information of the particular unit photo-detector 23a relative to all the unit photo-detectors 23a and on the particular wavelength.

(4) In the foregoing embodiments, the light amount adjusting device is provided for varying and adjusting the amount of light received by the light receiving section of the light transmitted through or reflected by the measured objects. Such a light amount adjusting device is dispensable.

(5) In the foregoing embodiments, the horizontal position adjusting device is provided to vary or adjust the light emitting position and light receiving position relative to the position for measurement along the direction in which these positions move toward or away from each other. This horizontal position adjusting device is dispensable, and the light emitting position and light receiving position relative to the position for measurement may be fixed.

(9) In the foregoing embodiments, the measured objects are transported by the transport conveyor to pass through the position for measurement. Instead, the measured objects may be placed in the position for measurement by a robot hand acting as the transporting device, or may be placed manually by the operator instead of the transporting device.

(10) In the foregoing embodiments, the sugar content and acid degree are cited as the inner quality of the measured objects M. Instead, other types of inner quality such as the information on taste or the like may be measured.

INDUSTRIAL UTILITY

The quality evaluation values of fruits and vegetables according to the present invention are usable in measuring the quality of fruits and vegetables such as oranges and apples, for example, including the inner quality like a sugar content or acid degree or the like, in a non-destructive condition.

The invention claimed is:

1. A quality evaluation apparatus for fruits and vegetables comprising a light emitting section which emits light to fruits or vegetables acting as one or more measured objects placed in a position for measurement, a light receiving section which receives transmitted light or reflected light from the measured object at a photo-detective sensor of charge storage type to obtain photo-detective information for quality evaluation, a transporting device for transporting the measured object via the position for measurement, and a control device which obtains inner quality information of the measured object based on the photo-detective information from the light receiving section and for controlling operation of the respective sections, wherein the control device repeatedly executes a charge storage discharge process for allowing the photo-detective sensor to store charges until a predetermined charge storage time elapses from start of charge storage and then releasing the charges stored in the photo-detective sensor until lapse of a predetermined discharge time when the measured object is not present in the position for measurement or when the photo-detective information for quality evaluation has already been obtained even if the measured object is present in the position for measurement, and wherein the control device allows the photo-detective sensor to release the charges stored therein until the predetermined discharge time elapses when the measured object transported by the transporting device reaches the position for measurement, and then executes a measurement charge storage process for storing charges in the photo-detective sensor to be used as the photo-detective information for quality evaluation until lapse of a predetermined measurement time.

2. The quality evaluation apparatus for fruits and vegetables as claimed in claim 1, further comprising an incidence switching device switchable between an open state for allowing the transmitted light or reflected light from the measured object to be received at the photo-detective sensor, and a closed state for preventing the light from being received at the photo-detective sensor, wherein the control device controls operation of the incidence switching device to switch from the closed state to the open state when the measured object reaches the position for measurement, and to reinstate the closed state after the open state is maintained until lapse of the predetermined measurement time.

3. The quality evaluation apparatus for fruits and vegetables as claimed in claim 1, wherein the transporting device transports the measured object as placed in particular positions on saucers, and wherein the control device includes a saucer detecting device for detecting that a forward end in a transporting direction of a saucer has reached a predetermined position, thereby to determine that the measured object has reached the position for measurement based on detection information from the saucer detecting device.

4. The quality evaluation apparatus for fruits and vegetables as claimed in claim 1, wherein the control device includes an object detecting member for detecting that a forward end in a transporting direction of the measured object transported by the transporting device has reached a position upstream of the position for measurement in the transporting direction, and a transporting distance measuring device for measuring a transporting distance of the measured object transported by the transporting device, and wherein the control device determines that the measured object has reached the position for measurement based on detection information from the transporting distance measuring device after detecting that the forward end of the measured object has reached the upstream position based on detection information from the object detecting device.

5. A quality evaluation apparatus for fruits and vegetables comprising:

a light emitting section for emitting near-infrared light to the measured object placed in a position for measurement;

a light receiving section for separating the light transmitted through or reflected from the measured object into rays and receiving the separated rays at a plurality of unit photodetectors; and a computing section for executing a quality evaluation process to obtain quality evaluation values of fruits or vegetables based on photo-detective information from the light receiving section obtained when the fruits or vegetables as one or more of the measured object are measured and on a calibration formula established in advance for quality evaluation of the fruits and vegetables;

the computing section being switchable to a state for executing a wavelength calibration process, instead of the quality evaluation process, to determine wavelengths received by the plurality of unit photodetectors, respectively, based on photo-detective information from the light receiving section obtained when a reference object for wavelength calibration is measured as the measured object which has characteristics in light transmission with respect to the near-infrared light of a specific wavelength;

wherein the calibration formula is established by using the photo-detective information with a resolution greater than a maximum resolution of the photo-detective information determined by the number of the plurality of unit photodetectors; and wherein the computing section executes the wavelength calibration process by using the photo-detective information with a resolution smaller than the resolution with which the calibration formula is established.

6. The quality evaluation apparatus for fruits and vegetables as claimed in claim 5, wherein the computing section executes the wavelength calibration process with the maximum resolution of the photo-detective information.

7. The quality evaluation apparatus for fruits and vegetables as claimed in claim 5, wherein the reference object for wavelength calibration has two or more specific wavelengths as the specific wavelength, and wherein the computing section determines a plurality of unit photodetectors receiving the plurality of specific wavelengths among the plurality of unit photodetectors in the wavelength calibration process, thereby to obtain the wavelengths received by the other unit photodetectors based on position information of the particular unit photodetectors with respect to all the unit photodetectors and the specific wavelengths.

8. The quality evaluation apparatus for fruits and vegetables as claimed in claim 5, wherein the light receiving section receives light of a predetermined wavelength band including the specific wavelengths at 1024 unit photodetectors, and wherein the computing section determines the wavelengths of the separated rays with a wavelength resolution of 0.8 nanometers or less in executing the wavelength calibration process, and determines the wavelengths of the separated rays with a wavelength resolution of 2 nanometers or more to obtain the quality evaluation values of the measured object in establishing the calibration formula.

9. The quality evaluation apparatus for fruits and vegetables as claimed in claim 5, further comprising a light amount adjusting device for varying and adjusting a light amount of light received by the light receiving section in the transmitted light or reflected light from the measured object.

10. The quality evaluation apparatus for fruits and vegetables as claimed in claim 5, further comprising a horizontal position adjusting device for varying and adjusting a light emitting position of the light emitting section and a light receiving position of the light receiving section relative to the position for measurement, respectively, along a direction in which these positions move toward or away from each other.

11. The quality evaluation apparatus for fruits and vegetables as claimed in claim 5, further comprising an incidence switching device switchable between an open state for allowing the transmitted light or reflected light from the measured object to be received at the unit photodetectors, and a closed state for preventing the transmitted light or reflected light from the measured object from being received at the unit photodetectors; and an operation control device for controlling operation of the respective sections;

wherein the operation control device controls operation of the incidence switching device to switch from the closed state to the open state when the measured object is placed in the position for measurement, and to reinstate the close stated after the open state is maintained until lapse of an open state maintaining time, and controls operation of the light receiving section to execute a measurement process for receiving the light from the measured object at the unit photodetectors while the incidence switching device is maintained in the open state.

12. The quality evaluation apparatus for fruits and vegetables as claimed in claim 5, further comprising a transporting device for transporting the measured object via the position for measurement.

13. The quality evaluation apparatus for fruits and vegetables as claimed in claim 12, further comprising a shading member for blocking stray light entering the unit photodetectors without being transmitted through the measured object, in the light emitted from the light emitting section, while allowing the measured object transported by the transporting device to pass through the position for measurement.

14. The quality evaluation apparatus for fruits and vegetables as claimed in claim 2, wherein the transporting device transports the measured object as placed in particular positions on saucers, and wherein the control device includes a saucer detecting device for detecting that a forward end in a transporting direction of a saucer has reached a predetermined position, thereby to determine that the measured object has reached the position for measurement based on detection information from the saucer detecting device.

15. The quality evaluation apparatus for fruits and vegetables as claimed in claim 2, wherein the control device includes an object detecting member for detecting that a forward end in a transporting direction of the measured object transported by the transporting device has reached a position upstream of the position for measurement in the transporting direction, and a transporting distance measuring device for measuring a transporting distance of the measured object transported by the transporting device, and wherein the control device determines that the measured object has reached the position for measurement based on detection information from the transporting distance measuring device after detecting that the forward end of the measured object has reached the upstream position based on detection information from the object detecting device.

* * * * *